(12) United States Patent
Choi et al.

(10) Patent No.: US 10,156,487 B2
(45) Date of Patent: Dec. 18, 2018

(54) FLEXIBLE TACTILE SENSORS AND METHODS OF MAKING

(71) Applicants: Jae-Won Choi, Copley, OH (US); Erik Daniel Engeberg, Boca Raton, OH (US); Morteza Vatani, Akron, OH (US); Ho-Chan Kim, Andong-si (KR); Thomas Swiger, Hudson, OH (US)

(72) Inventors: Jae-Won Choi, Copley, OH (US); Erik Daniel Engeberg, Boca Raton, OH (US); Morteza Vatani, Akron, OH (US); Ho-Chan Kim, Andong-si (KR); Thomas Swiger, Hudson, OH (US)

(73) Assignee: The University of Akron, Akron, OH (US)

( * ) Notice: Subject to any disclaimer, the term of this patent is extended or adjusted under 35 U.S.C. 154(b) by 0 days.

(21) Appl. No.: 15/270,626

(22) Filed: Sep. 20, 2016

(65) Prior Publication Data

US 2017/0059426 A1    Mar. 2, 2017

Related U.S. Application Data

(63) Continuation-in-part of application No. PCT/US2015/021729, filed on Mar. 20, 2015.

(60) Provisional application No. 61/955,863, filed on Mar. 20, 2014, provisional application No. 62/043,461, filed on Aug. 29, 2014.

(51) Int. Cl.
| | |
|---|---|
| *G01L 1/22* | (2006.01) |
| *G06F 3/047* | (2006.01) |
| *A61B 5/103* | (2006.01) |
| *G01L 5/00* | (2006.01) |

(52) U.S. Cl.
CPC .......... *G01L 1/2293* (2013.01); *A61B 5/1036* (2013.01); *G01L 5/00* (2013.01); *G06F 3/047* (2013.01); *G06F 2203/04102* (2013.01); *G06F 2203/04104* (2013.01)

(58) Field of Classification Search
CPC ....... G01L 1/2293; G01L 5/00; A61B 5/1036; G06F 3/047; G06F 2203/04102; G06F 2203/04104
USPC ..................................................... 73/862.632
See application file for complete search history.

(56) References Cited

U.S. PATENT DOCUMENTS

| | | | |
|---|---|---|---|
| 6,878,255 B1 * | 4/2005 | Wang ................. | G01N 27/4473 204/451 |
| 2008/0054875 A1 * | 3/2008 | Saito .................... | A61B 5/1172 324/71.5 |

(Continued)

*Primary Examiner* — Max Noori
(74) *Attorney, Agent, or Firm* — Renner, Kenner, Greive, Bobak, Taylor & Weber Co. LPA

(57) ABSTRACT

A tactile sensor includes a first insulating layer having a first array of electrically conductive strips embedded therein and extending in a first direction. An intermediate layer of conductive soft polymer material is positioned above the first insulating layer and the first array of said electrically conductive strips. A second insulating layer having a second array of electrically conductive strips embedded therein, which extend in a second direction which is different than the first direction, is positioned above the intermediate layer. The first array of electrically conductive strips are connected to the second array of electrically conductive strips, and both the first and second array of electrically conductive strips are also connected to an impedance measuring device.

52 Claims, 15 Drawing Sheets

(56) References Cited

U.S. PATENT DOCUMENTS

| | | | |
|---|---|---|---|
| 2009/0148967 A1* | 6/2009 | Wodnicki | H01L 22/14 438/17 |
| 2013/0134410 A1* | 5/2013 | Kim | H01L 51/0039 257/40 |
| 2014/0293150 A1* | 10/2014 | Tang | G06F 3/044 349/12 |

* cited by examiner

FLEXIBLE TACTILE SENSORS AND METHODS OF MAKING

CROSS-REFERENCE TO RELATED APPLICATIONS

This application is a continuation-in-part of international application No. PCT/US2015/021729 filed on Mar. 20, 2015, which claims priority from U.S. Provisional Application No. 61/955,863 filed on Mar. 20, 2014 and from U.S. Provisional Application No. 62/043,461 filed on Aug. 29, 2014, the contents of which are incorporated herein by reference.

FIELD OF THE INVENTION

The embodiments of the present invention relate to force measuring sensors and methods of fabricating the same. Particularly, the embodiments of the present invention relate to the use of force sensors that utilizes multiple sensing elements that are arranged in an array to measure changes in force across a surface. More particularly, the embodiments of the present invention relate to a force sensor having an array of individual force sensing elements that are each surrounded by a resilient base, such as an insole of a shoe.

BACKGROUND

There have been notable advances in the design and development of artificial robotic hands over the last several decades. The Utah/M.I.T. hand was developed over twenty years ago with three fingers and a thumb. More recently, the Gifu hand and the Shadow Hand have been developed with high levels of dexterity. Because the dexterity of these artificial hands is approaching that of human hands, tactile sensing is very important for the development of intelligent grasp control algorithms. Tactile sensing is also very important in upper limb prosthetics, where a number of mechanical advances have also been recently made. For example, the i-Limb has four fingers and a thumb with one motor for each digit. The Smarthand and Michelangelo hand also have five fingers.

One general problem for upper limb amputees is that they lack proprioceptive feedback about the grip force applied by their prostheses. For this reason, amputees are more likely to drop grasped objects because they do not know exactly how tightly the object is grasped. This is corroborated by recent surveys from amputees which indicate their desire for a level of automatic grasped object slip prevention. However, the detection and prevention of grasped objects from slipping is a difficult problem in general that is important not only for prosthetic hands but also for autonomous robots.

There are several approaches to enhance the flexibility of tactile sensors. The flexibility of silicon-diaphragm sensors can be increased through the incorporation of polymers during the fabrication process. Mounting the sensors on a flexible substrate or using polyimide layers as a connecting material between silicon-diaphragm sensors can also increase the flexibility of the sensors. Another approach is the use of compressible and flexible conductive sheets as a sensing material to increase the size and flexibility of tactile sensors. With this previous approach, flexible sheets are sandwiched by conductive strips. Although these sensors provide good flexibility in a large area, their response, spatial resolution, and sensor size on a large area are limited. Control of dimensions of sensors and sensor elements during the fabrication process is another limitation Therefore, there is a need for a force sensor that includes an array of discrete force sensing elements that is able to achieve any desired level of force sensing resolution. In addition, there is a need for a force sensor that includes an array of force sensing elements, which is capable of wireless communication with a remote computer system to provide real-time, or near real-time telemetry.

SUMMARY

In a first embodiment, the present invention provides a tactile sensor comprising: a first insulating layer having a first array of electrically conductive strips embedded therein and extending in a first direction; an intermediate layer of conductive soft polymer material positioned above said first insulating layer and first array of said electrically conductive strips; and a second insulating layer having a second array of electrically conductive strips embedded therein and extending in a second direction which is different than said first direction positioned above said intermediate layer, wherein said first array of electrically conductive strips are connected to said second array of electrically conductive strips, and wherein both the first and second array of electrically conductive strips are connected to an impedance measuring device.

In a second embodiment, the present invention provides a tactile sensor as in the first embodiment, wherein said first and second arrays of electrically conductive strips include conductive nanostructures dispersed in a flexible support material.

In a third embodiment, the present invention provides a tactile sensor as in either the first or second embodiment, wherein the conductive soft polymer is selected from the group consisting of ionic-liquid polymer, particle based soft conductive polymers, and soft polymers having intrinsic conductivity.

In a fourth embodiment, the present invention provides a tactile sensor as in any of the first through third embodiments, wherein the conductive soft polymer is an ionic liquid polymer selected from the group consisting of 1-ethyl-3-methylimidazolium tetrafluoroborate (EMIBF4) with the glass transition temperature (Tg) of −95.15° C.; 1-ethyl-3-methylimidazolium bis(trifluoromethylsulfonyl) imide (EMITFSI) with the Tg of −98.15° C.; and 1-butylpyridinium tetrafluoroborate (BPBF4) with the Tg of −66.7° C.

In a fifth embodiment, the present invention provides a tactile sensor as in any of the first through fourth embodiments, wherein the ionic liquid polymer contains from 0.01 or more to 10 or less weight percent (wt %) of ionic liquid, based upon the total weight of the intermediate layer.

In a sixth embodiment, the present invention provides a tactile sensor as in any of the first through fifth embodiments, wherein the ionic liquid polymer contains from 0.05 or more to 7.5 or less weight percent (wt %) ionic liquid, based upon the total weight of the intermediate layer.

In a seventh embodiment, the present invention provides a tactile sensor as in any of the first through sixth embodiments, wherein the ionic liquid polymer contains from 0.5 or more to 5 or less weight percent (wt %) ionic liquid, based upon the total weight of the intermediate layer.

In an eighth embodiment, the present invention provides a tactile sensor as in any of the first through seventh embodiments, wherein the ionic liquid polymer contains from 1 or more to 2.5 or less weight percent (wt %) ionic liquid, based upon the total weight of the intermediate layer.

In a ninth embodiment, the present invention provides a tactile sensor as in any of the first through eighth embodiments, wherein the ionic liquid polymer is a pressure sensitive polymer.

In a tenth embodiment, the present invention provides a tactile sensor as in any of the first through ninth embodiments, wherein said second direction of said second array of electrically conductive strips is off of parallel as compared to said first direction of said first array.

In an eleventh embodiment, the present invention provides a tactile sensor as in any of the first through tenth embodiments, wherein said conductive nanostructures are selected from the group consisting of conductive nanowires, carbon nanotubes, and graphene.

In a twelfth embodiment, the present invention provides a tactile sensor as in any of the first through eleventh embodiments, further comprising said carbon nanotubes are selected from the group consisting of multi-walled carbon nanotubes or single wall carbon nanotubes.

In a thirteenth embodiment, the present invention provides a tactile sensor as in any of the first through twelfth embodiments, wherein said electrically conductive strips contain from 0.01 wt % to 20 wt % carbon nanotubes and wherein said carbon nanotubes have an average length from 300 nanometers to 30 microns.

In a fourteenth embodiment, the present invention provides a tactile sensor as in any of the first through thirteenth embodiments, wherein said impedance measuring device is a Wheatstone bridge.

In a fifteenth embodiment, the present invention provides a tactile sensor as in any of the first through fourteenth embodiments, wherein said first insulating layer and said second insulating layer is stretchable.

In a sixteenth embodiment, the present invention provides a tactile sensor as in any of the first through fifteenth embodiments, wherein said first insulating layer and said second insulating layer comprise material selected from group consisting of elastomers, polymers, and thermoplastics.

In a seventeenth embodiment, the present invention provides a tactile sensor as in any of the first through sixteenth embodiments, wherein the elastomers are selected from the group consisting of polyepoxides rubber, natural polyisoprene, synthetic polyisoprene, polybutadiene, chloroprene rubber, butyl rubber, styrene-butadiene rubber, nitrile rubber, ethylene propylene rubber, epichlorohydrin, polyacrylic rubber, silicone rubber, fluoresilicone, fluoroelastomers, perfluorelastomers, polyether block amines, chlorosulfonated polyethylene, ethyl ene-vinyl acetate, thermoplastic elastomer, polyurethane, and mixtures thereof.

In an eighteenth embodiment, the present invention provides a tactile sensor as in any of the first through seventeenth embodiments, wherein said material of said first insulating layer can be the same or different than the material of the second insulating layer.

In a nineteenth embodiment, the present invention provides a tactile sensor as in any of the first through eighteenth embodiments, wherein the tactile sensor detects: applied force such as normal and shear forces, the proximity of the applied force, slip events, slip direction, slip speed, slip velocity, temperature changes, rolling contact, the shape of an object in contact with said tactile sensor, and vibration.

In a twentieth embodiment, the present invention provides a method of making a tactile sensor, comprising: pouring an insulating soft polymer material into a mold to form a first layer of insulating soft polymer material; curing the first layer of insulating soft polymer material; depositing a mixture of prepolymer and carbon nanotubes on the first layer of insulating soft polymer material to form a first array of conductive strips; curing the first array conductive strips; pouring a conductive soft polymer material onto the first layer of insulating soft polymer material and conductive strips to cover the first layer of insulating soft polymer material and conductive strips to form an intermediate layer of conductive soft polymer material; curing the intermediate layer of conductive soft polymer material; depositing a mixture of prepolymer and carbon nanotubes on the intermediate layer of conductive soft polymer material to form a second array of conductive strips; curing the second array conductive strips; pouring an insulating soft polymer material to cover the second array of conductive strips to form a second layer of insulating soft polymer material; and curing the second layer of insulating soft polymer material.

In a twenty-first embodiment, the present invention provides a method of making a tactile sensor as in the twentieth embodiment, wherein the mixture of prepolymer and carbon nanotubes is deposited via a micro-dispensing head, or screen printing.

In a twenty-second embodiment, the present invention provides a method of making a tactile sensor as in the twentieth and twenty-first embodiments, wherein the mixture of prepolymer and carbon nanotubes is directly cured into strips using UV light or thermal curing.

In a twenty-third embodiment, the present invention provides a method of making a tactile sensor as in the twentieth through twenty-second embodiments, wherein the conductive soft polymer is selected from the group consisting of ionic-liquid polymer, particle based soft conductive polymers, and soft polymers having intrinsic conductivity.

In a twenty-fourth embodiment, the present invention provides a method of making a tactile sensor as in the twentieth through twenty-third embodiments, wherein the conductive soft polymer is an ionic-liquid polymer selected from the group consisting of 1-ethyl-3-methylimidazolium tetrafluoroborate (EMIBF4) with the Tg of −95.15° C.; 1-ethyl-3-methylimidazolium bis(trifluoromethylsulfonyl)imide (EMITFSI) with the Tg of −98.15° C.; and 1-butylpyridinium tetrafluoroborate (BPBF4) with the Tg of −66.7° C.

In a twenty-fifth embodiment, the present invention provides a sensor to measure force, the sensor comprising: at least one sensing element including: a first electrode; a sensing layer positioned adjacent to the first electrode, wherein the sensing layer comprises a polymerized acrylic semiconductor material; and a second electrode positioned adjacent to the semiconductor material, wherein when force is applied to the sensing element, the sensing layer generates a corresponding voltage value that is output across the first and second electrodes.

BRIEF DESCRIPTION OF THE DRAWINGS

The application file contains at least one drawing executed in color. Copies of this patent or patent application publication with color drawing(s) will be provided by the Office upon request and payment of the necessary fee.

DETAILED DESCRIPTION

The present invention relates to tactile sensors and to methods of making them. In some embodiments, the present invention further relates to tactile sensors that are developed using direct-write technology to lay down, within a flexible medium, multiple conductive strips of electrically conductive carbon nanotubes mixed within a polymer matrix.

Figure 1A:
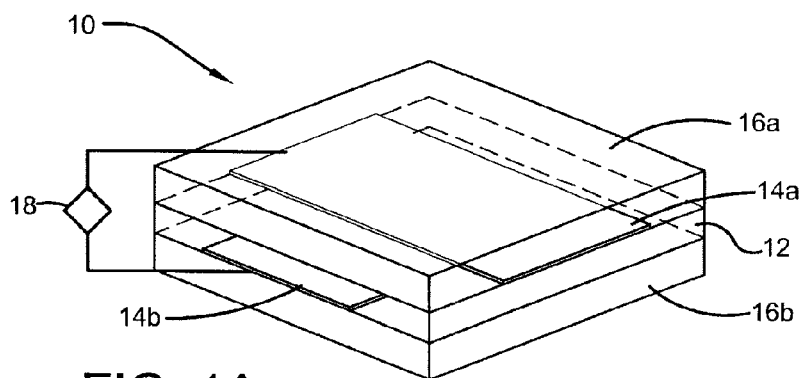
FIG. 1A is a schematic view of a tactile sensor comprising two overlapping conductive strips, two insulating layers, and an intermediate layer located between the two overlapping conductive strips.
Figure 1B:
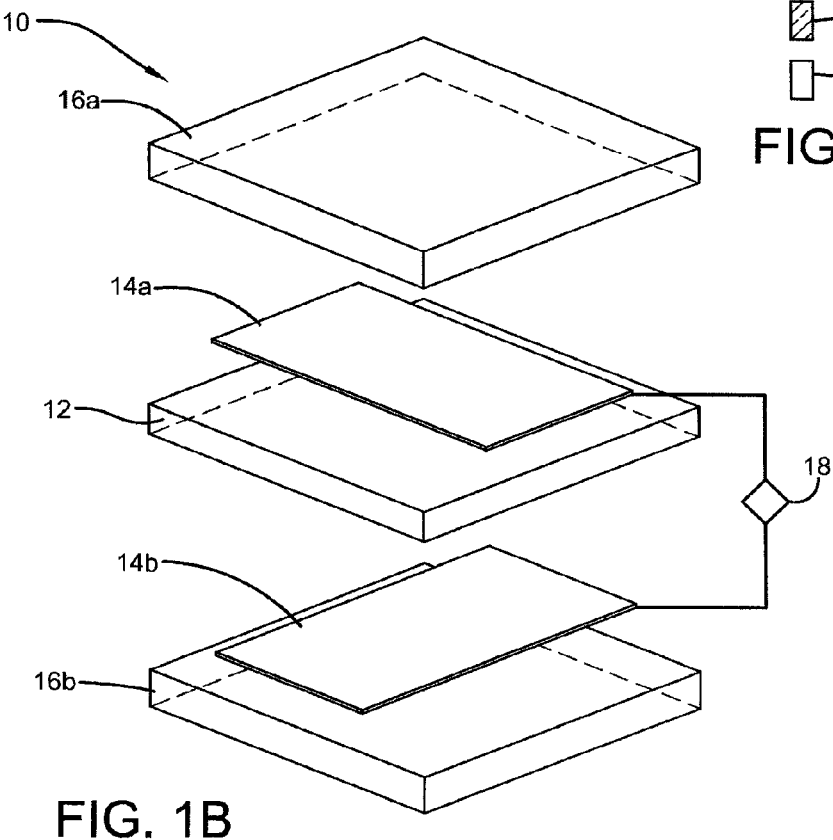
FIG. 1B is an exploded schematic view of the tactile sensor of FIG. 1A.

With reference to FIGS. 1A and 1B, one embodiment of the present invention provides a tactile sensor 10 comprising electrically conductive strips 14a and 14b, two insulating layers 16a and 16b, and an intermediate layer 12. The electrically conductive strips 14a and 14b can be aligned as straight strips, two-dimensional curved strips, three-dimensional curved strips, wavy patterned strips. The electrically conductive strips can also be aligned into any designed pattern.

Conductive strip 14a is connected to conductive strip 14b and to an impedance measuring device 18. In some embodiments the impedance measuring device also includes a source of power. In yet other embodiments, in addition to being connected to an impedance measuring device 18, the conductive strips 14a and 14b are also connected to a power supply (not shown). In some embodiments, the impedance measuring device is a half Wheatstone bridge, which includes a voltage source in series with a resistor. The impedance measuring device can be any such device known in the art. Impedance measuring devices work by applying a known or measured force to each strip while simultaneously measuring the change in impedance of the intermediate layer 12 (or the voltage output from each half Wheatstone bridge). Then, the change in resistance or voltage is related back to the applied force. This relation back is then used to calculate a new, unknown force.

Figure 2:
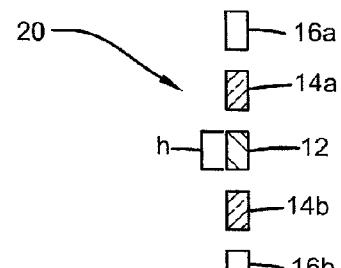
FIG. 2 is a schematic representation of a cross-sectional view of the relationship between two overlapping conductive strips, two insulating layers, and an intermediate layer.

The embodiment in FIGS. 1A and 1B shows an intermediate layer 12 having two layers of electrically conductive strips 14a and 14b. Although this embodiment only shows two arrays/layers of electrically conductive strips, sensors of the present invention can have any number of arrays/layers of electrically conductive strips. The area of overlap of an upper and lower conductive strip is known as a taxel. FIG. 2 shows the taxel 20 formed where conductive strips 14a and 14b overlap. As shown in FIG. 2, the intermediate layer 12 is located between the conductive strips 14a and 14b. The intermediate layer 12 has a height h and it separates the two conductive strips 14a and 14b so that the two conductive strips 14a and 14b are not in direct contact with one another.

The taxel 20 formed by connecting the conductive strips 14a and 14b to each other has better sensing capabilities. In this type of the sensor, the change in the height h of the intermediate layer 12 due to the deformation of the sensor is very sensitive to the changes in resistance. Any changes in resistance of the conductive strips 14a and 14b are negligible when the resistance of the intermediate layer 12 is maintained to be much greater than that of the conductive strips 14a and 14b. The pressure compresses the sensor and thus the height h of the intermediate layer 12 becomes smaller. Since the original height h is small, usually less than 500 um, when the pressure disappears, the value of the height h when compressed returns to the initial value very quickly. On the other hand, in prior art sensors that do not connect conductive strips to one another, such sensors detect changes in resistance of the strip. A pressure is applied; which stretches a strip horizontally, which equates to a change in resistance. There is a large deformation, and it takes time for the elongated strip to return to its original length. In addition, with such prior art sensors, the strip or strips are surrounded by an elastomer, and the restoration time when the strip returns to the original status is dependent on the surrounding elastomer. This causes a serious bottleneck because when there is no pressure, there is supposed to be no change in resistance. The sensor setup as shown in FIGS. 1-5, is not affected by the surrounding materials and strips, so it has much better sensing capabilities.

In some embodiments, there is only one insulating layer, and in other embodiments, there are multiple insulating layers. The insulating layer or layers are formed from non-conductive flexible material while the intermediate layer should have a conductivity of between about 50MΩ and about 500MΩ. The insulating layer(s) needs to be formed of a non-conductive material so that the insulating layer(s) do not interfere with the conduction of the conductive strips 14a and 14b, as will be appreciated to a better degree after further disclosures herein. In some embodiments, suitable materials for the insulating layers are selected from elastomers, polymers, and thermoplastics. In some embodiments, elastomers may be selected from polyepoxides rubber, natural polyisoprene, synthetic polyisoprene, polybutadiene, chloroprene rubber, butyl rubber, styrene-butadiene rubber, nitrile rubber, ethylene propylene rubber, epichlorohydrin, polyacrylic rubber, silicone rubber, fluoresilicone, fluoroelastomers, perfluorelastomers, polyether block amines, chlorosulfonated polyethylene, ethylene-vinyl acetate, thermoplastic elastomer, and polyurethane, or mixtures thereof. In one or more embodiments, the insulating layer(s) is made from polyurethane. When multiple layers are employed to create the sensor, the layers may be the same or different.

In some embodiments, the intermediate layer 12 is formed from a conductive soft polymer material. The conductive soft polymer material can be selected from the group consisting of ionic liquid based soft polymers, particle based soft conductive polymers, and soft polymers having intrinsic conductivity. An example of a soft conductive polymers include carbon nanotubes (CNTs) in polydimethylsiloxane (PDMS) and an example of soft polymers having intrinsic conductivity include TangoPlus FullCure™ 930), polyacetylene, polypyrrole, polyaniline, and there copolymers. In one embodiment, the conductive soft polymer material of the intermediate layer is an ionic liquid based soft polymer.

Ionic liquids (ILs) are defined as a salt in the liquid state, consisting of ions and short-live ion pairs. IL's are a green media due to their superior characteristics of non-flammability, non-volatility, high ion conductivity, high thermal stability, and high chemical stability. When IL's are used in an embodiment, they are strictly restricted to salts whose melting points are relatively low, such as lower than about 100° C. In some embodiments the IL's are selected from 1-ethyl-3-methylimidazolium tetrafluoroborate (EMIBF4) with the Tg of −95.15° C.; 1-ethyl-3-methylimidazolium bis(trifluoromethylsulfonyl)imide (EMITFSI) with the Tg of −98.15° C.; and 1-butylpyridinium tetrafluoroborate (BPBF4) with the Tg of −66.7° C., which can be in-situ polymerizable. Higher ionic conductivity can be generated from high ion mobility, high ion density and low polymer glass transition temperature (Tg).

In one or more embodiments, the IL-polymer used as the intermediate layer comprise from 0.01 or more to 10 or less weight percent (wt %) IL based upon the total weight of the polymer used in the intermediate layer, in another embodiment, from 0.05 or more to 7.5 or less wt % IL, in another embodiment, from 0.5 or more to 5 or less wt % IL, and in yet another embodiment, from 1 or more to 2.5 or less wt % IL, based upon the total weight of the intermediate layer.

In one or more embodiments, the IL-polymer is also a pressure sensitive polymer.

The conductive strips 14a and 14b comprise conductive nanostructures dispersed in a flexible support material. As used herein, the term "conductive nanostructure" is meant to include conductive nanowires, carbon nanotubes (CNTs), and graphene. In one embodiment, the flexible support material is a polymer. The polymer may be virtually any flexible polymer. In some embodiments, the conductive strips have a width of from 5 microns or more to 3 mm or less. In some embodiments, the conductive strips have a width of from 10 microns or more to 2 mm or less. In some embodiments, the conductive strips have a width of 10 microns or more to 1 mm or less.

Embodiments of the present invention use CNTs for their mechanically strong, electrically conductive, and piezoresistive properties. The carbon nanotubes can be single-walled or multi-walled. Single-walled nanotubes are carbon nanotubes where the tube has only one layer. Multi-walled nanotubes are carbon nanotubes where the tube has more than one layer. These nanotube structures and additional nanotube structures are known by those skilled in the art.

In some embodiments, the CNTs have exceptionally high aspect ratios of from 500 or more to 1000 or less. In some embodiments, the CNTs have high Young's modulus of 0.64 TPa or higher. In some embodiments, the CNTs have a high stiffness of 1,000 GPa or higher. In some embodiments, the CNTs have high tensile strength of 100 GPa or higher. In some embodiments, the CNTs have a bulk density of 1.4 $g/cm^3$ or lower. In some embodiments, the CNTs have a bulk density in the range of about 0.15 $g/cm^3$ to about 1.3 $g/cm^3$. In other embodiments, the CNTs have the ability to withstand large strain rates of from 6% or more to 10% or less. In addition to their outstanding physical and mechanical properties, CNTs show exceptional electrical properties. Depending on their radius or chirality, CNTs can be metallic or semiconducting, and both are suitable for use in accordance with the present invention.

Metallic CNTs have exceptionally low electrical impedance of around 0.5Ω, and piezoresistivity (gauge factor around 600 to 1000 in a small scale). Dispersing CNTs into a polymer matrix reinforces the polymer in order to ameliorate the mechanical properties, and also embeds a highly conductive electrical element within the polymer.

The length of the CNTs can have an effect on the tunneling resistance of the conductive strips, and, for more sensitive sensors, it is preferred that the CNTs be short to produce more junctions between neighboring CNTs along the length of the strips. In some embodiments, the CNTs have an average length from 300 nanometers or more to 30 microns or less. In other embodiments, the CNTs have an average length from 500 nanometers or more to 20 microns or less. In other embodiments, the CNTs have an average length from 1 micron or more to 5 microns or less.

In some embodiments, the carbon nanotubes have a purity of more than 85 wt %, diameter from 10 to 30 nm, and length from 5 to 20 μm.

In one or more embodiments, the conductive structures are metal nanowires. The metal nanowires can be made from copper, silver, gold, or mixtures thereof. The metal nanowires can be made from any conductive metal that is known in the art as being able to form nanowires.

The length of the nanowires can have an effect on the tunneling resistance of the conductive strips, and, for more sensitive sensors, it is preferred that the nanowires be short to produce more junctions between neighboring nanowires along the length of the strips. In some embodiments, the nanowires have an average length from 300 nanometers or more to 30 microns or less. In other embodiments, the nanowires have an average length from 500 nanometers or more to 20 microns or less. In other embodiments, the nanowires have an average length from 1 micron or more to 5 microns or less.

The graphene additions are generally planar and will have length and width dimensions. In some embodiments, the length and width is from 300 nanometers or more to 30 microns or less. In other embodiments, the length and width is from 500 nanometers or more to 20 microns or less. In other embodiments, the length and width is from 1 micron or more to 5 microns or less.

The prepolymer used to form the carbon nanotube-filled polymer can be any stretchable prepolymer that is capable of mixing with carbon nanotubes and showing conductivity after mixing and curing. The prepolymer is mixed with carbon nanotubes before being polymerized to form the electrically conductive strips 14a and 14b.

The prepolymer is mixed with a curing agent in order to cure the solution into strips. The curing agent can be thermally initiated by adding heat, or can be initiated by light, such as with UV, visible, or infrared light, depending on the photoinitiator.

For ease of manufacture, in one or more embodiments, the prepolymer is a material that is photocurable or photocrosslinkable. Photocrosslinking properties provide a way to directly cure the deposited materials, whereas in the conventional direct write or printed electronics, a post-baking process is required. In one embodiment, the present invention provides a sensor wherein a post-baking process is not required.

In particular embodiments, the prepolymer is selected from the groups consisting of cyclic trimehylolpropane formal acrylate, Cyclic Trimehylolpropane Formal Acrylate mixed with Acrylate Ester, Tango Plus (a commercially available photocurable material from Objet Co.), and mixtures thereof.

In some embodiments, the prepolymer is selected from propoxylated neopentyl glycol diacrylate, propoxylated glyceryl triacrylate, aromatic urethane acrylate, urethane acrylate, cyclic trimehylolpropane formal acrylate, acrylate easter, aromatic monoacrylate, ethoxylated bisphenon a dimethacrylate, and mixtures thereof. In some embodiments, the prepolymer is selected from commercial 3D Printing photopolymers such as Objet TangoBlackPlus Fullcure980, TangoPlus FullCure930, TangoBlack FullCure970, and TangoGray FullCure950, and mixtures thereof.

In one or more embodiments, the prepolymer is prepared by blending a photoinitiator with a monomer or oligomer in order to aid in the process of photocuring the prepolymer. The photoinitiator may be chosen from 2,2-dimethoxy-2-phenylacetophenone, acyl phosphine oxides, bisacryl phosphine oxides, bis(2,4,6-trimethylbenzoyl) phenylphophine oxide, benzoin ethyl ether, 5,7-diiodo-3-butoxy-6-fluorone, and mixtures thereof. In one or more embodiments, commercial 3D printing photopolymers can be used without using a photoinitiator. In one or more embodiments, commercial 3D printing photopolymers are mixed with an additional photoinitiator when it they are mixed with a monomer or oligomer.

In one or more embodiments, the conductive strips comprise from 0.01 or more to 20 or less weight percent (wt %) nanostructures, in another embodiment, from 0.05 or more to 15 or less weight percent (wt %) nanostructures, in another embodiment, from 0.5 or more to 10 or less weight percent (wt %) nanostructures and in yet another embodiment, from 1 or more to 5 or less weight percent (wt %) nanostructures, based upon the total weight of the conductive strips.

In one or more embodiments, the conductive strips comprise 0.01 or more weight percent (wt %) nanostructures, in another embodiment, 0.05 or more weight percent (wt %) nanostructures, in another embodiment, 0.5 or more weight percent (wt %) nanostructures and in yet another embodiment, 1 or more weight percent (wt %) nanostructures, based upon the total weight of the conductive strips.

In one or more embodiments, the conductive strips comprise 10 or less weight percent (wt %) nanostructures, in another embodiment, 7.5 or less weight percent (wt %) nanostructures, in another embodiment, 5 or less weight percent (wt %) nanostructures and in yet another embodiment, 3 or less weight percent (wt %) nanostructures, based upon the total weight of the conductive strips.

The conductive strips 14a and 14b form the electrode of the sensor 10 while the intermediate layer 12 forms the sensing aspect of the sensor 10. Impedance and voltage can be measured across the strips 14a and 14b and intermediate layer 12, by the impedance measuring device 18. Strip 14a, intermediate layer 12 and strip 14b form a series circuit. The measuring device 18 measures impedance and voltage within the circuit.

In one embodiment, the sensor 10 of the present invention can be biomimetic in the sense that they can have mechanical compliance similar to human fingertips. The sensor 10 can also be used to detect force at distinct locations of applied pressure and slip. Furthermore, by examining the relative timing of the force signals from adjacent conductive strips, multiple sensors 10 can be used to detect slip and the direction that slip occurs. This is similar to the way that people can determine the direction that forces are applied through the relative timing of action potentials from mechanoreceptors within the fingertip.

The principle for detecting slip is based on the fact that high frequency mechanical vibrations occur when one object slips against another object. Different objects exhibit different vibrations in the frequency domain. Pressing an object against the surface of a tactile sensor (without slip) and sliding the same object against the surface of the sensor (to simulate slip) results in a difference in frequency. The difference in the frequency domain between these two tactile events can be characterized with a fast Fourier transform (FFT). The FFT can be performed with signal processing software on the raw, unfiltered voltage recorded from the output of a Wheatstone half bridge to illustrate the differences between the slip and nonslip events in the frequency domain.

Sensors of the present invention can also distinguish between slip and nonslip events. In one embodiment, sensors of the present invention allow the force to be measured at distinct locations on the surface of the sensor with low cross talk.

Utilizing a taxel setup 20 within a sensor 10, wherein two or more electrically conductive strips overlap each other, and having the two conductive strips 14a and 14b of the taxel 20 connected to one another, as opposed to a single strip in a sensor that is connected to itself, gives the sensor 10 greater sensitivity to applied forces. FIGS. 6-9 show the response of a sensing element utilizing the taxel setup of the present invention versus a sensing element utilizing a single strip setup. The two sensing elements were placed under sinusoid force with frequencies varying from 0.3 Hz to 2.5 Hz being applied to the sensor. As the graphs show, the sensing element of the present invention is much more sensitive to the applied force as compared to a sensing element utilizing a single strip.

In one or more embodiments comprising multiple layers of electrically conductive strips, the direction of the strips in the next layer is non-parallel to the direction of the strips in the preceding layer. In other embodiments, the direction of the strips in the next layer is orthogonal to the direction of the strips in the preceding layer.

Figure 3:
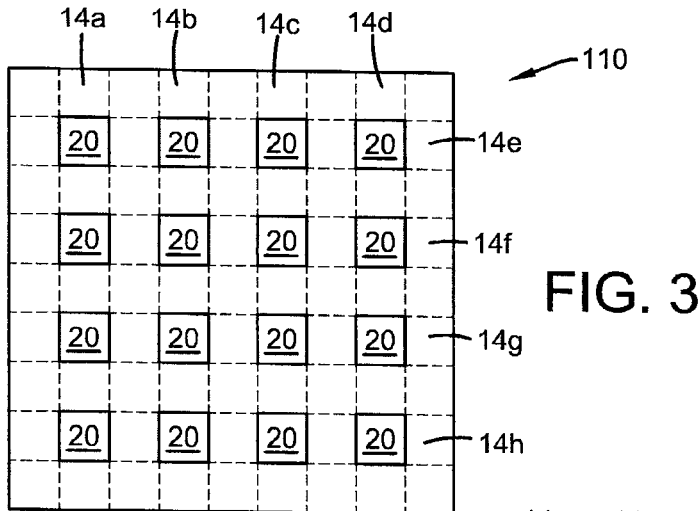
FIG. 3 is a schematic top view of a tactile sensor comprising multiple electrically conductive strips overlapping with one another.
Figure 4:
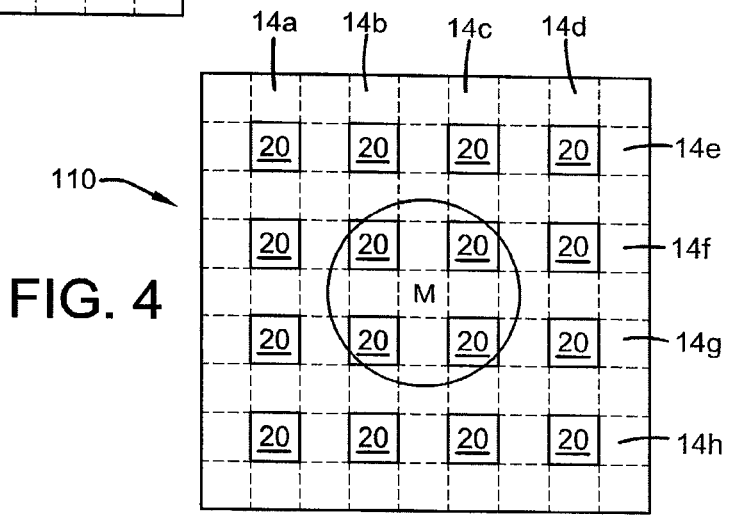
FIG. 4 is a schematic top view of the tactile sensor of FIG. 3 wherein the sensor has an object thereon.

FIG. 3 shows another embodiment, similar to FIGS. 1A and 1B, wherein the tactile sensor 110 has multiple electrically conductive strips 14a-14d which overlap with multiple electrically conductive strips 14e-14h. With such a setup, the location of a force can be noted in more than one dimension. It should be noted that one row of conductive strips is considered as input connected to a power supply (14a-14d), (power supply not shown) while the other row (another layer) is considered as the output (14e-14h) and is connected to an impedance measuring device (not shown). At each sampling time, only one of the input conductive electrodes is connected to the power supply, for example (14a). At same time all the output signals (14e-14h) are connected to their individual measuring device 18. As a result, for example, 4 taxels 20 (combination of 14a with (14e-14h) are measured separately. The other taxels are measured at other sampling times. This will help to detect multiple touch as well as shape characterization. For example, with reference to FIG. 4, an object M placed on the sensor 110 such that it presses on adjacent strips 14b and 14c and now also presses on adjacent strips 14f and 14g. This causes an impedance change in the portion of the intermediate layer 12 of the taxel 20 located at the overlap of 14b and 14f, in the portion of the intermediate layer 12 of the taxel 20 located at the overlap of 14c and 14f, in the portion of the intermediate layer 12 of the taxel 20 located at the overlap of 14b and 14g, and in the portion of the intermediate layer 12 of the taxel 20 located at the overlap of 14c and 14g, first the two taxels (14b-14f) and (14b-14g) are measured and then the (14c-14f) and (14c-14g) are measured using the scanning process explained above. As a result the impedance change in all taxels are measured separately and thus the object can be characterized as being positioned somewhere between strips 14a and 14d as well as somewhere between strips 14e and 14h.

Figure 5:
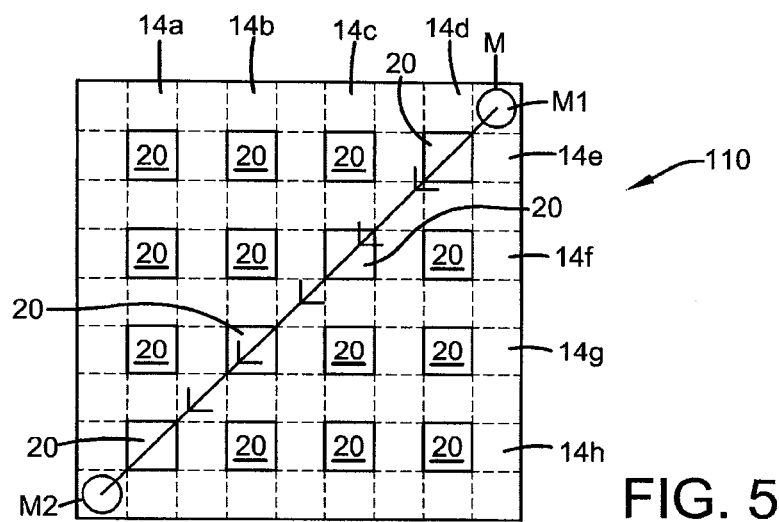
FIG. 5 is a schematic top view of the tactile sensor of FIG. 3 wherein the sensor has an object moving thereacross.
Figure 6:
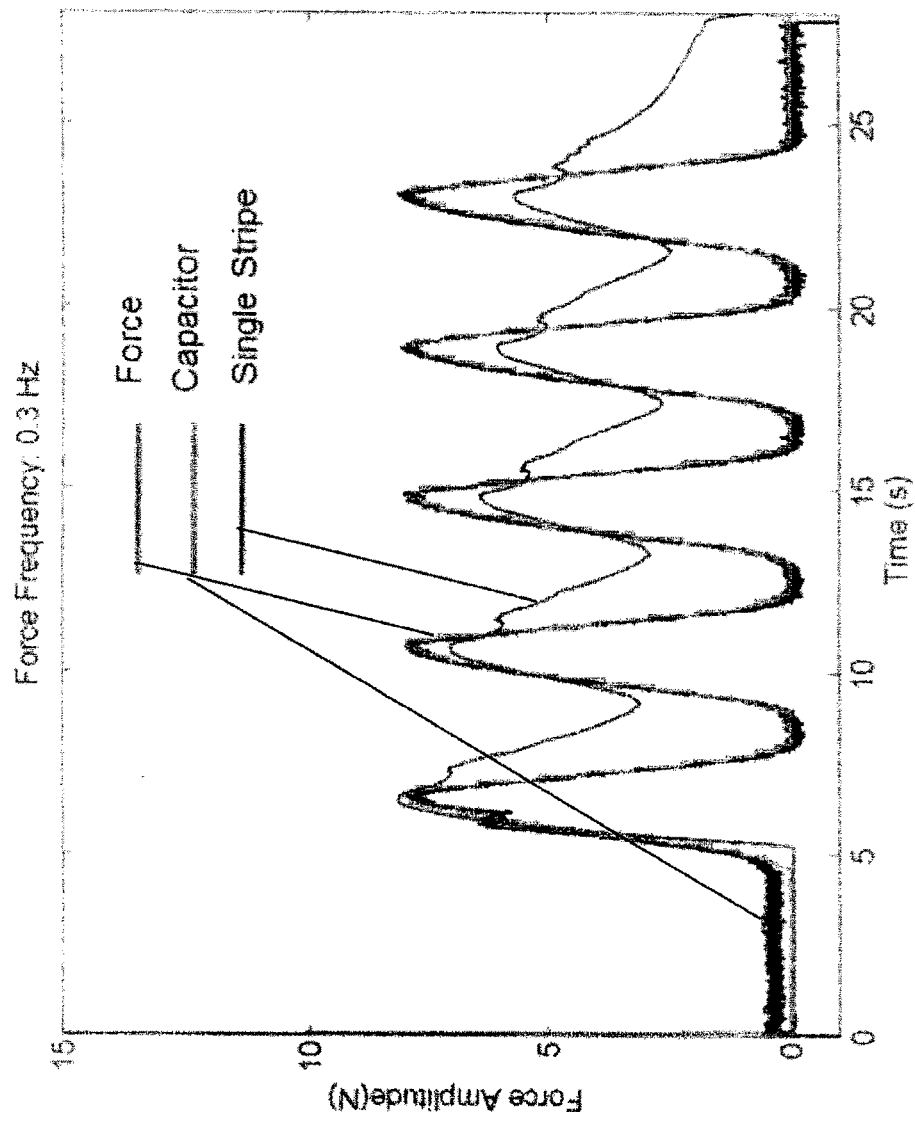
FIG. 6 is a graph showing the tactile sensor of the present invention and a single stripe tactile sensor detecting an external pressure of 0.3 Hz.
Figure 7:
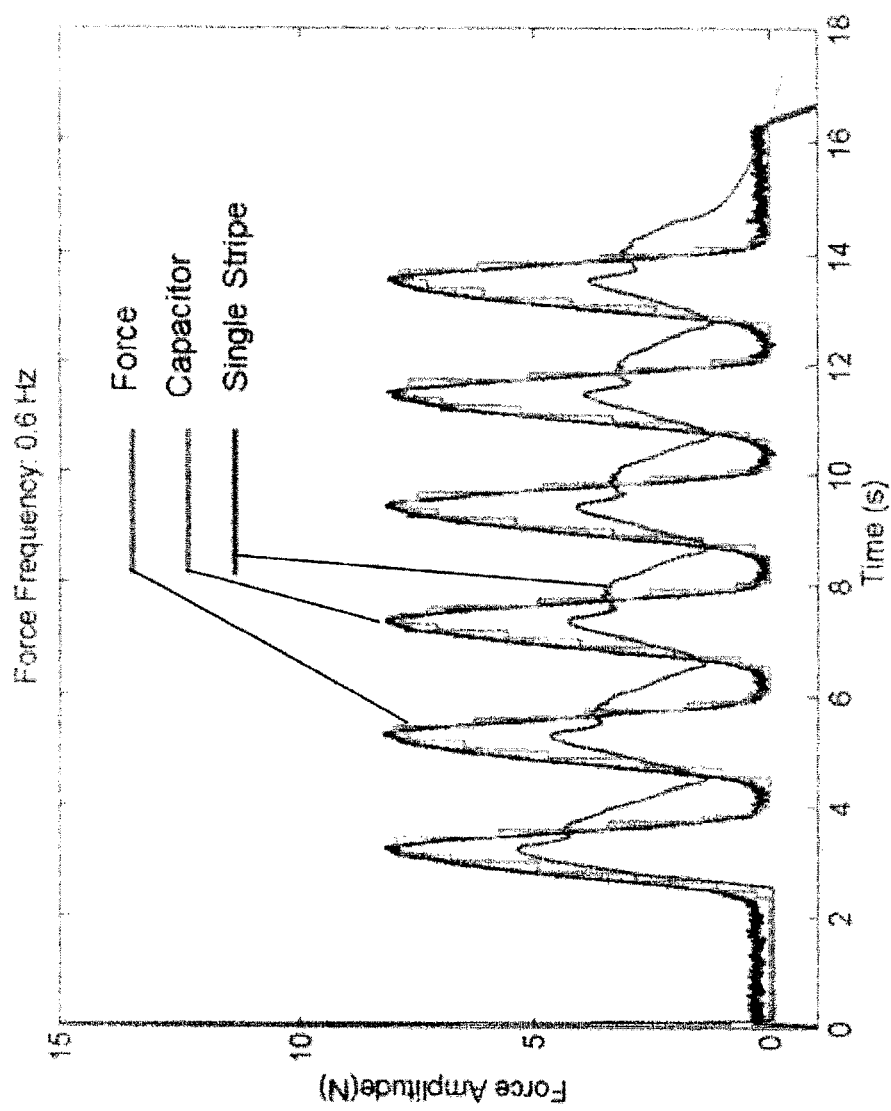
FIG. 7 is a graph showing the tactile sensor of the present invention and a single stripe tactile sensor detecting an external pressure of 0.6 Hz.
Figure 8:
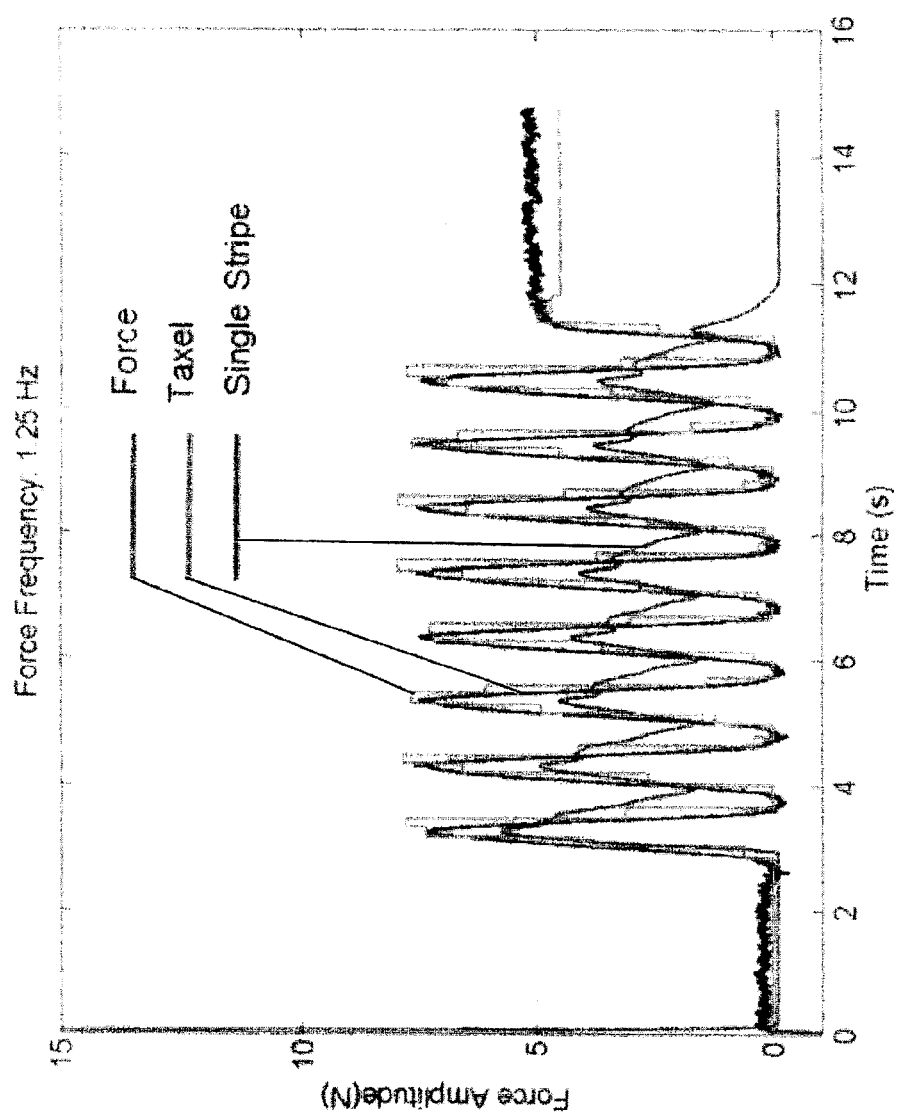
FIG. 8 is a graph showing the tactile sensor of the present invention and a single stripe tactile sensor detecting an external pressure of 1.25 Hz.
Figure 9:
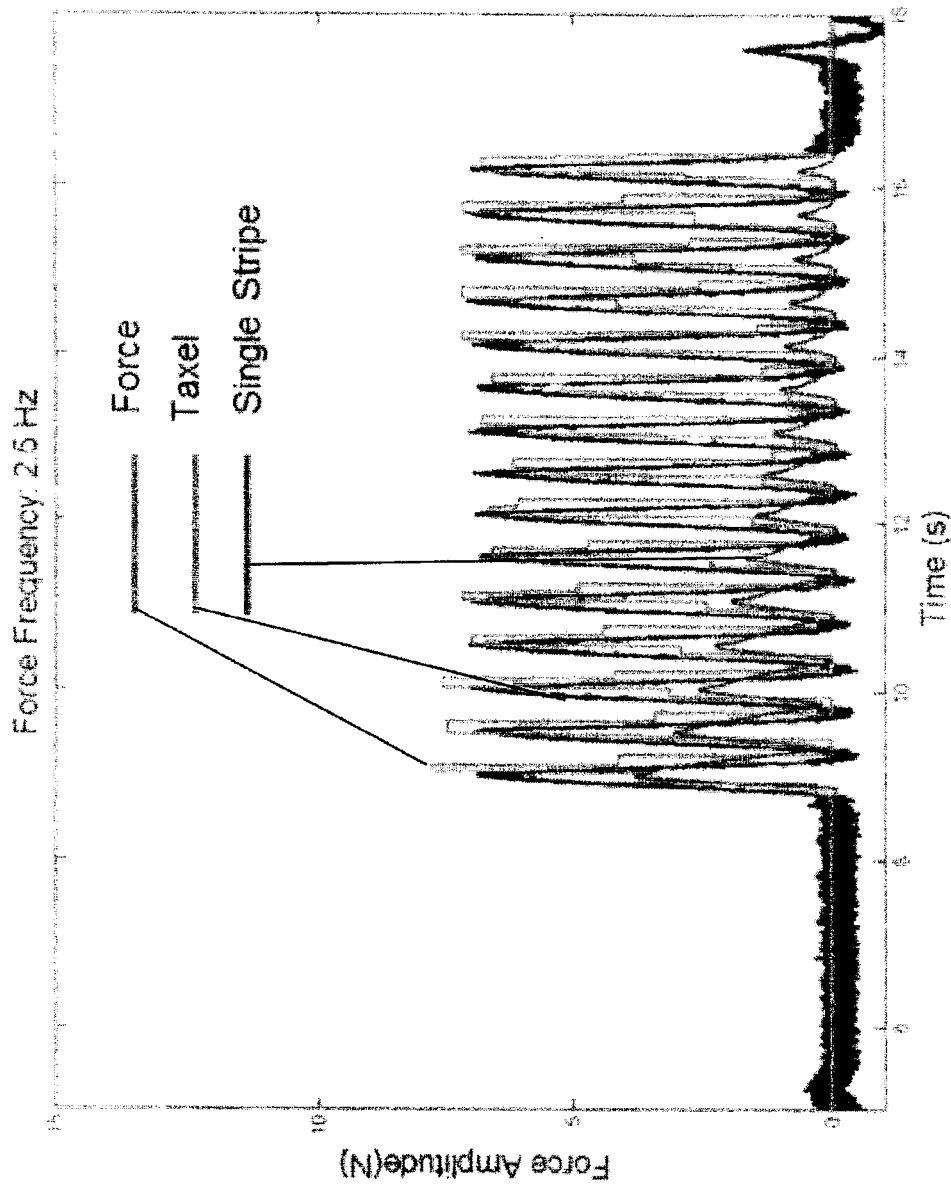
FIG. 9 is a graph showing the tactile sensor of the present invention and a single stripe tactile sensor detecting an external pressure of 2.5 Hz.

Further, by measuring impedance at each individual taxel 20, the direction of a slip event can be determined by the sensor 110. With reference to FIG. 5, an object M sliding on the sensor from position M1 to position M2 will cause an impedance change at the different taxels 20 created by the overlap of strips 14a-14d and 14e-14h at different times. First causing a change at the taxel 20 created by the overlap of 14d and 14e, then at the taxel 20 created by the overlap 14c and 14f, then at the taxel 20 created by the overlap 14b and 14g, and finally at the taxel 20 created by the overlap 14a and 14h. Thus it can be determined that the object is moving or "slipping" downwardly. This is valuable data, as, in the area of robotics, a slip event can be cause for increasing the grip force.

Although the sensors embodied in FIG. 1 through FIG. 5 are generally rectangular, sensors of the present invention can take any shape. Sensors of the present invention can be cylindrical, conical, spherical, or combinations thereof. Sensors of the present invention can take any designed three-dimensional shape.

One embodiment of the present invention provides a method of producing a tactile sensor by placing a conductive intermediate polymeric layer between two electrically conductive strips in a flexible medium. In a particular embodiment, a tactile sensor is produced by first forming a first layer of insulating elastomeric material, then placing at least one electrically conductive strip on the first layer of insulating elastomeric material, then laying down a conductive intermediate polymeric layer so as to fully cover the first layer of insulating elastomeric material and the electrically conductive strip, then placing at least one additional electrically conductive strip on the conductive intermediate polymeric layer, and then forming a second layer of insulating elastomeric material so as to fully cover the additional electrically conductive strip and the conductive intermediate polymeric layer. Sensors of the present invention can have any number of layers of electrically conductive strips and any number of elastomeric shells. The other processes to make the sensor is to selectively place and pattern the conductive intermediate polymeric layer at taxel place and cover the rest of area with of insulating elastomeric material.

In one or more embodiments, the first layer of insulating elastomeric material is formed by placing an appropriate elastomeric material into a mold to form a first layer. This first layer is then cured to set its form.

In one or more embodiments, the first layer of insulating elastomeric material can be formed using any curable elastomers in ambient conditions. In one or more embodiments, the first layer of insulating elastomeric material can be formed using room temperature and no vacuum.

After formation of the first layer, the at least one conductive strip is laid down. The at least one conductive strip comprise conductive nanostructures dispersed in a flexible support material. The conductive nanostructure is selected from the group consisting of include conductive nanowires, carbon nanotubes (CNTs), graphene, and or combination thereof. First, the flexible support material and the conductive nanostructure mixture must be made. The flexible support material comprises a combination of suitable prepolymer and a photoinitiator. The conductive nanostructure/flexible support mixture is formed by combining the selected conductive nanostructure with the selected prepolymer and photoinitiator where necessary. The mixture is then mixed until the conductive nanostructure is sufficiently dispersed within the flexible support mixture. This mixture is patterned onto the first layer to form the at least one conductive strip.

In one embodiment, the photoinitiator is first blended with the prepolymer using a magnetic stirrer. Then, the selected conductive nanostructures are dispersed into the prepolymer solution.

In one or more embodiments, the mixture is sonicated to improve the dispersion of the selected conductive nanostructure. During sonication, ultrasound propagation in the solution results in growth of cavities. The implosion of these cavities leads to violent and localized release of energy which can separate and disperse individual conductive nanostructures from bundles and agglomerates, where cavitation and wave propagation are directly related to the viscosity of liquid. Non-uniform energy release distribution during sonication leads to weak and non-homogeneous dispersion especially in medium to high viscosity liquid. To overcome this problem and prevent the localization of the high-energy ultrasound field around the tip of the sonicator, a combination of sonicator and magnetic stirrer can be used to globally disperse the conductive nanostructures in the prepolymer. In one or more embodiments, the prepared solution can be degassed under a vacuum. In one embodiment, the solution is degassed for 5 hours. In some embodiments, the mixture is sonicated (Q700, Qsonica, Newtown, Conn.) for 90 min and filtered using a 200 micron filter (Sterlitech, Kent, Wash.).

The conductive strips can be placed using any technology known in the art. The conductive strips are ultimately cured and can be cured by any technology known in the art. In one or more embodiments, the deposited materials are directly cured. In one or more embodiments, the conductive strips are cured using UV, visible, or infrared light depending on the photoinitiator selected. Other methods of curing the conductive strips include thermal curing using a thermal initiator, such as 2,2'-azobis(2-methyl-propionamidine) dihydrochloride, 2,2'-azobis(2-methylpropionitrile), benzoyl peroxide, and mixtures thereof.

In one embodiment, the conductive strips are placed using direct-write technology. Direct-write (DW) technology is a maskless process to create conductive patterns on virtually any surface. With this technology, translation mechanisms are utilized to position a dispensing head to extrude a conductive material on a substrate which forms a functional wire pattern.

A direct-write system comprises a micro-dispensing tip and a means for directly curing the dispensed material. Direct-write applications include robotic tactile sensors and soft molding.

In one embodiment, sensors of the present invention are prepared by a computer controlled DW system using a screw-driven micro-dispensing head (PCD3, GPD Global, Grand Junction, Colo.) installed on a high precision xyz translation stage with a 500 nm resolution (Aerotech, Pittsburgh, Pa.). Then, a four-leg optical fiber with a high-power UV lamp (OmniCure S2000, Lumen Dynamics Group Inc., Ontario, Canada) can be installed around the dispensing head to directly cure the dispensed material.

One schematic of the developed DW system comprises the xyz stage, micro-dispensing device, and curing system. Controlling the speed of the xyz stage, the gap distance between the tip and substrate, and the dispensing speed regulated by the input voltage of the dispensing head can be used to form a precise and consistent shape of deposited sensor elements.

In one or more embodiments, the electrically conductive strips or wires possess a consistent width throughout the length of each strip. Dispensing parameters directly affect the size and resolution of the dispensed material. Several parameters affect the ability to maintain continuous and smooth flow of the material delivered from the dispensing tip to the substrate surface. The width of the strips decreases as the flow rate increases and too low flow rate does not create consistent and continuous line widths. Another parameter is the translation speed. Translation speed is the speed of the stage underneath the dispensing tip. In one embodiment the translation speed is from 20 mm/sec or more to 30 mm/sec or less. In one embodiment the translation speed is 15 mm/sec or more and in other embodiments the translation speed is 35 mm/sec or less. High flow rates and slow translation speeds result in inconsistent line widths of conductive elements. Excessively fast translation speed and slow fluid flow rate also creates discontinuous or inconsistent line widths.

Variation of the gap distance between the tip and the substrate also causes inconsistent line widths. Where polyurethane material is used as the substrate, the surface is flexible with a relatively broad surface area. Here, small variations in gap distance are unavoidable. However, the use of a highly accurate and uniform substrate and/or real-time distance measurement device installed in the dispensing head would be a method to reduce this variation in gap distance, thereby giving more consistency to the line width.

Material agglomeration generated during the dispersion process is another source of line width variation. The agglomerated material sometimes partially occluded the tip and resulted in a pressure change in the tip. This pressure change caused inconsistent line widths. The material agglomeration can be improved by using a better material dispersion process and chemicals such as surfactants and/or dispersants.

Several sets of preferred parameters can be chosen to achieve consistent line widths. In one embodiment, the parameters are a flow rate from about 0.16 ml/V·min or more to 0.18 ml/V·min or less, translation speed of about 20 mm/s, and a line width of about 0.8 mm.

After curing the at least one conductive strip, an Ionic-Liquid polymer is laid down and cured to form the intermediate layer. Preferably the intermediate layer between the at least one conductive strip and the at least one additional conductive strip has a thickness/height from at least about 100 microns or more to at least about 5 mm or less, in other embodiments, from at least about 1 mm to at least about 5 mm and, in other embodiments, from at least about 1 mm or more to at least about 2 mm or less.

After formation of the intermediate layer, the at least one additional conductive strip is laid down. The at least one additional conductive strip comprises conductive nanostructures dispersed in a flexible support material. The conductive nanostructure and flexible support material can either be the same or different than the conductive nanostructure and flexible support material of the first at least one conductive strip.

After curing the at least one additional conductive strip, the second layer of insulating elastomeric material can be formed using any curable elastomers in ambient conditions.

In one embodiment, this invention provides a method to produce polymeric tactile sensors using direct write (DW) and soft molding technologies. One particular method of producing a tactile sensor is:

(a) pour stretchable insulating soft polymer material into a mold;

(b) cure the insulating soft polymer material to form a first insulating elastomeric material layer;

(c) deposit stretchable and photocrosslinkable/thermocrosslinkable prepolymer filled with carbon nanotubes (CNTs) via a micro-dispensing head;

(d) cure the prepolymer filled with CNTs to form conductive strips or patterns using UV light, or thermal curing;

(e) add a layer of soft IL-polymer material to cover the first insulating elastomeric material layer and the conductive strips or patterns;

(f) cure the soft IL-polymer material to form the conductive intermediate polymeric layer;

(g) deposit stretchable and photocrosslinkable/thermocrosslinkable prepolymer filled with carbon nanotubes (CNTs) via a micro-dispensing head;

(h) cure the prepolymer filled with CNTs to form conductive strips or patterns using UV light, or thermal curing;

(i) pour stretchable insulating soft polymer material to cover the conductive strips or patterns and the conductive intermediate polymeric layer; and (j) cure the insulating soft polymer material to form a second insulating elastomeric material layer.

IV. Sensor

This material design enables the fabrication of mechanically compliant and electrically conductive tactile sensors. Advantageously, tactile sensors of the present invention are mechanically compliant to facilitate delicate grasping procedures and to be more suited for a wider range of applications.

A sensor can be calibrated by applying a known or measured force to each overlapping point of two strips, also known as a taxel, while simultaneously measuring the change in impedance of the intermediate layer between the strips (or the voltage output from each half Wheatstone bridge). Then, the change in resistance or voltage is related to the applied force. In one embodiment, a sensor is calibrated by pressing on a taxel with a LSP-10 load cell (Transducer Techniques, Temecula, USA). The applied force is measured while the resultant voltage change from each half bridge is measured with Simulink. Sensors of the present invention are able to measure force at distinct points on the surface and can distinguish between slip and nonslip tactile events.

Sensors of the present have many beneficial applications. These applications include any robotic system where control of force is required (e.g. assembly lines), diagnostics (e.g. determining if antilock brakes prevent slip), prosthetic limbs, conformal or wearable electronics (e.g. head-band thermometer), biomedical instruments and measurement (e.g. foot pressure measurement for customized shoes, body-type collection chair, bedsore-free bed), electronics embedded in structural components, and implantable electronics with biocompatible materials.

Sensors of the present invention can be used to measure both shear and normal forces.

EXAMPLES

Example 1

Materials

To fabricate flexible robotic tactile sensors, commercially available photocurable resin (Tangoplus full cure 930, Objet Geometries, MA., USA, which is both flexible and tough, was used as a flexible polymer to make a prepolymer solution to fabricate electrically conductive strips. In this solution, multi-walled carbon nanotubes (MWCNTs) were dispersed using an ultrasonic bath. Industrial-grade MWCNTs (purity>85 wt %) was purchased from NanoLab (Waltham, Mass.), which has an average diameter of 10-30 nm and length of 5-20 µm. To harden the extruded material, a thermal initiator was used. RIGONOX 125C75, Akzo Nobel Functional Chemicals, LLC, IL) was added into the solution and mixed using the high speed mixer for 5 min.

Preparation of a MWCNTs-polymer Solution for Conductive Strips:

To make electrically conductive strips 5 wt % of noncovalent functionalized MWNTs dispersed into the FullCure® 930 TangoPlus. The weighted amount of MWNTs were noncovalently functionalized through their dispersion into a solution of Triton X100 (Sigma-Aldrich, Milwaukee, Wis., USA) in dimethylformamide (DMF, Sigma-Aldrich, Milwaukee, Wis., USA). The ratio of CNT to Triton X100 was selected as 1:350. The solution was blended using a globally dispersion method. In this method a sonicator (Q700, Qsonica, Newtown, Conn., USA) with a power of 700 W, frequency of 20 kHz, and amplitude of 50% for 20 min in pulse mode (1 min on, 10s off) was used in presence of an external magnetic stirrer. During the sonication, ultrasound propagation in the solution results in growth of cavities. The implosion of these cavities leads to violent and localized release of energy which can separate and disperse individual CNTs from bundles and agglomerates, where cavitation and wave propagation are directly related to the viscosity of liquid. Non-uniform energy release distribution during sonication leads to weak and non-homogeneous dispersion especially in medium to high viscosity liquid. To overcome this problem and prevent the localization of the high-energy ultrasound field around the tip of the sonicator, a combination of sonicator and magnetic stirrer was used to globally disperse the CNTs in the polymer matrix After the functionalization process, the prepared solution of DMF/MWNTs was blended with the TangoPlus resin using the same process for five more minutes. Then, the prepared MWNT/prepolymer was placed on a hot plate magnetic stirrer (VWR 10×10 ALU Hotplate 120V, VWR, IL) at 100° C. for 48 h to completely evaporate the solvent. After the dispersion and evaporation, the solution was again mixed using a high speed mixer (DAC 150.1 FVZ-K, FlackTek Inc. Landrum, S.C.) at 2500 rpm for 1 hr. 4 wt % of thermal initiator (TRIGONOX 125C75, Akzo Nobel Functional Chemicals, LLC, IL) was added into the solution and mixed using the high speed mixer for 5 min.

Ionic Polymer for Conductive Intermediate Layer.

A highly flexible photocurable monofunctional monomer (SR 278, Sartomer America, PA) as diluent was mixed with Tangoplus 930 with ratio of 1:4 using a magnetic stirrer for 30 min to prepare the main matrix of IL-polymer. 1 wt % of 1-ethyl-3-methylimidazolium tetrafluoroborate (EMIBF4, Sigma-Aldrich, Milwaukee, Wis., USA) was mixed into the solution using the high speed mixer at 2500 rpm for 5 min.

Fabrication of Robotic Tactile Sensors:

A direct-write system was developed using a micro-dispensing head (PCD3, GPD Global, Grand Junction, Colo.) installed on a precision xyz stage with resolutions of 500 nm. The PCD3 dispensing head consists of a lead-screw and stepper motor, featuring the exact volumetric dispensing due to the precise screw-driven extrusion. The stepper motor runs by changing voltage (0-10 V) so that the material can be dispensed with various extrusion speeds. The direct-write system comprised a xyz translation mechanism, a micro-dispensing unit, and a UV lamp.

A tactile sensor was created with two layers of conductive strips where there were 4 conductive strips in first layer and 6 conductive strips in the second layer with a conductive IL-polymer between them and embedded between two layers of insulating material. Once all the wires were created, they were cured using heat at 120° C. Then, the cured wires were covered with a soft IL-polymer material so that the wire pattern was encapsulated by the soft IL-polymer material. After curing the IL-polymer the second layer of conductive strips was printed and cured at 120 C, and then they were covered using another layer of insulating material. The fabricated robotic tactile sensor for this experiment had 24 taxels. The fabricated sensor is comparably flexible in both wires and substrate.

Adjusting the dispensing parameters is critical to achieve a desired feature size and spatial resolution for conductive strips. It is believed that the profile shape, accuracy and consistency of the deposited material are affected by several parameters. Beside the inherent parameters of DW systems (e.g. tip geometry, and screw geometry) or fluid properties, the tip size, fluid flow rate (dispensing speed), translation speed (feed rate), and gap distance between the tip and surface are crucial factors which must be accurately adjusted. Experimental data was used help choose the parameters.

A developed direct-write system was used to dispense the MWCNT/polymer composite over the insulating layer. The created wires were then cured by heat.

The tactile sensor was calibrated by pressing on each taxel with a LSP-10 load cell (Transducer Techniques, Temecula, USA) to measure the force while the resultant voltage change from each half bridge was measured with Simulink. To further evaluate the sensor, experiments were performed to illustrate the ability to measure force at distinct points on the surface and the ability to distinguish between slip and nonslip tactile events.

The principle for detecting slip is based on the fact that high frequency mechanical vibrations occur when one object slips against another object. These vibrations were characterized in the frequency domain for a variety of objects: steel, aluminum, plastic, and human fingertips. Those objects were first pressed against and removed from the surface of the tactile sensor (without slip) and then also slid against the surface of the sensor. The difference in the frequency domain between the two classes of tactile events was characterized with a fast Fourier transform (FFT). The FFT was performed using signal processing software on the raw, unfiltered voltage recorded from the output of the Wheatstone half bridge to illustrate the differences between the slip and nonslip events in the frequency domain.

Finally, the relative timing between the spikes in force detected in each conductive strip cannot be used as an indicator of slip because that could easily be caused by rolling motion (where there is no slip) or by an irregularly shaped object in contact with the sensor. For example, if the tactile sensor was pressed against a conical object, the timing of the force signals would sequentially increase as each part of the sensor made contact with the side of the cone. This could be mistaken as slip unless the frequency domain was analyzed for vibrations caused by slip.

Evaluation of the Tactile Sensor:

The impedance of each conductive strip in the tactile sensor is on the order of 10-100KΩ while the resistivity of intermediate layer of the soft IL-polymer material is in order of 50-500MΩ. Resistors of comparable impedance were placed in series with each conductive strip in one layer of conductive strips while conductive strips in the other layer are connected separately using a multiplexer to a power supply to create a half Wheatstone Bridge for each circuit. The voltage from each half-bridge was measured with using signal processing software. The sample rate was 1 kHz.

To evaluate the tactile sensor, several tests were performed to illustrate the ability to measure force at distinct points on the surface and the ability to distinguish between slip and nonslip tactile events.

Figure 10:
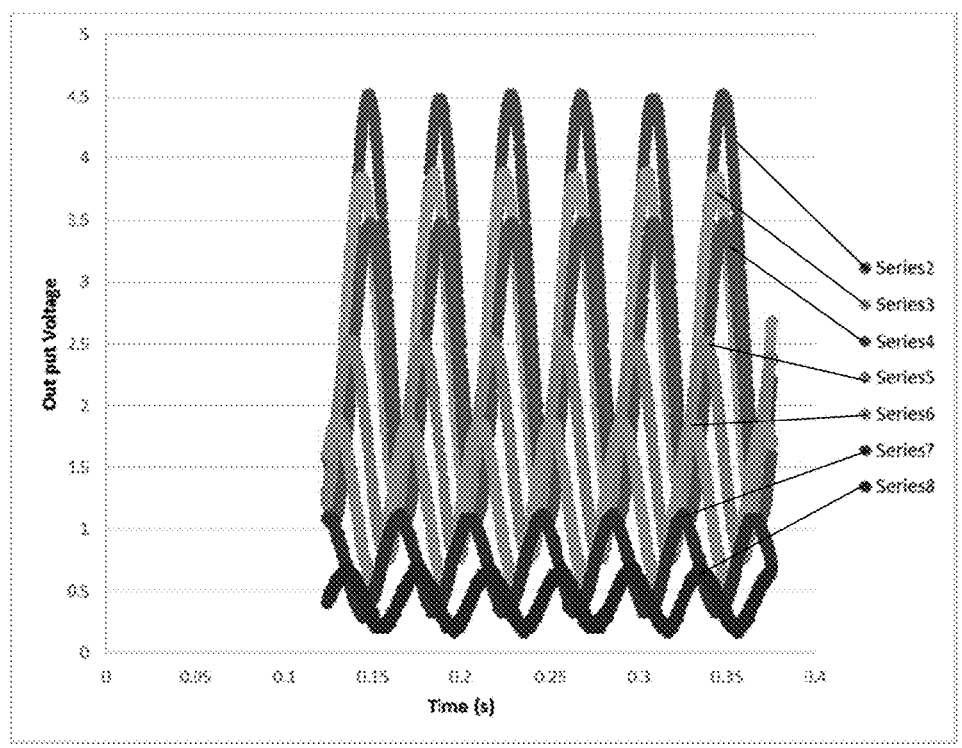
FIG. 10 is a graph showing the measured voltage from half Wheatstone bridge, wherein the resistor in series 2 is 90 M-ohm, the resistor in Series3 is 30 M-ohm, the resister in series 4 is 20 M-ohm, the resister in series 5 is 8.2 M-ohm, the resistor in series 6 is 4.7 M-ohm, the resister in series 7 is 2.2 M-ohm, and the resister in series 8 is 1.2 M-ohm.
Figure 11:
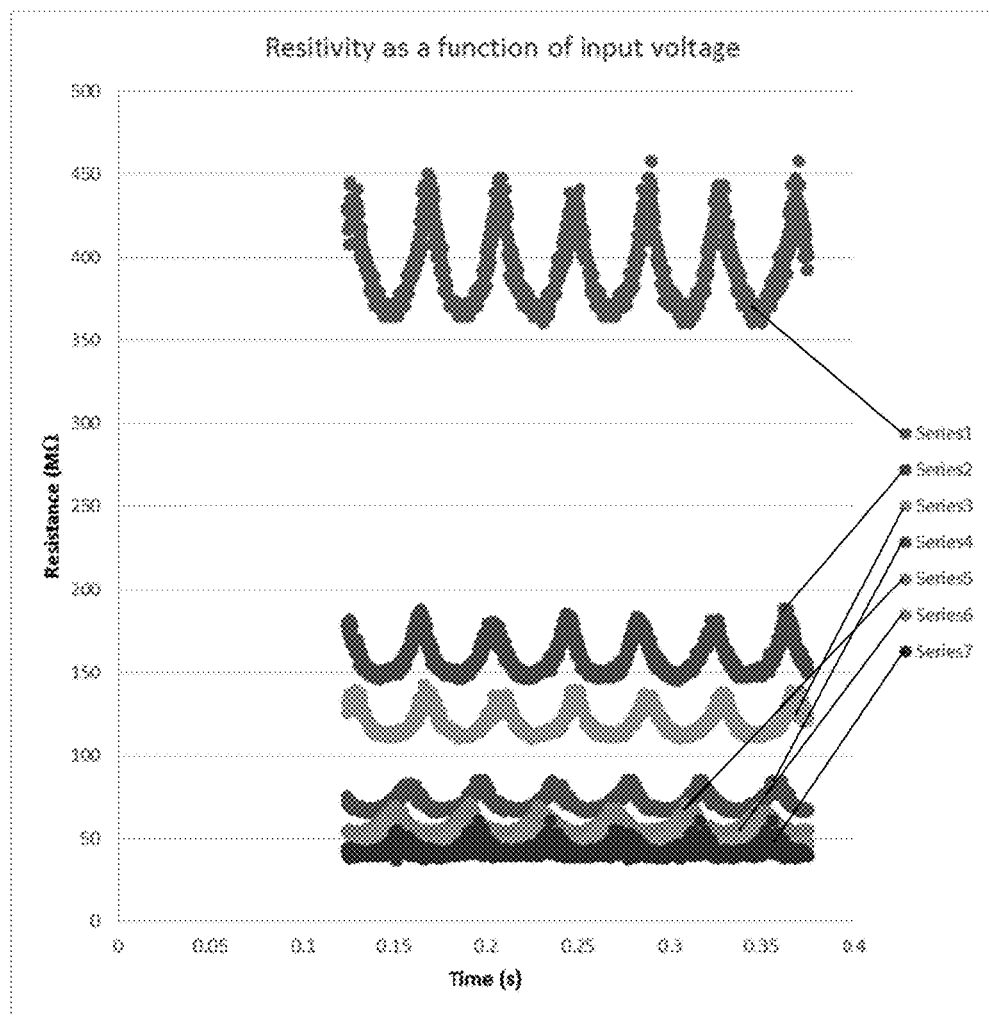
FIG. 11 is a graph of the data of FIG. 10 which shows the resistivity as a function of input voltage.

Test 1:

In test 1, different periodic input voltages were applied to a taxel. The output voltages were measured using a oscilloscope. The results, as shown in FIG. 10, show that the IL-polymer is electrical filed dependent. FIG. 11 is a graph of the data of FIG. 10 which shows the resistivity as a function of input voltage. FIG. 11 shown that the resistivity of the soft IL-polymer material intermediate layer depends on the generated electrical field and as a result, if the electrical field changes, so will the resistivity. This shows that the electrical field can be changed by changing the distance between two electrodes (conductive strips).

Test 2

In Test 2, a probe was repeatedly placed on the tactile sensor and removed several times to change the distance between electrodes. The applied force was also measured simultaneously to calibrate the sensor. The signal was recorded using signal processing software and graphs that were compiled from this test showed the accurate capability of the taxels in measuring force.

Test 3:

In Test 3, a circular object was rolled over the surface of a multi taxel sensor of the present invention. The relative timing of the resultant voltage spikes of three adjacent conductive strips was measured to demonstrate two things. First, that force can be measured at distinct locations on the surface of the tactile sensor and second, that the relative timing of the forces can be used to indicate the direction of rolling motion. The graphs that were created indicating the location of contact, the direction of contact, and the speed of motion of the object, which was indicated by the timing between the impedance change on each taxel.

Test 4

Figure 12:
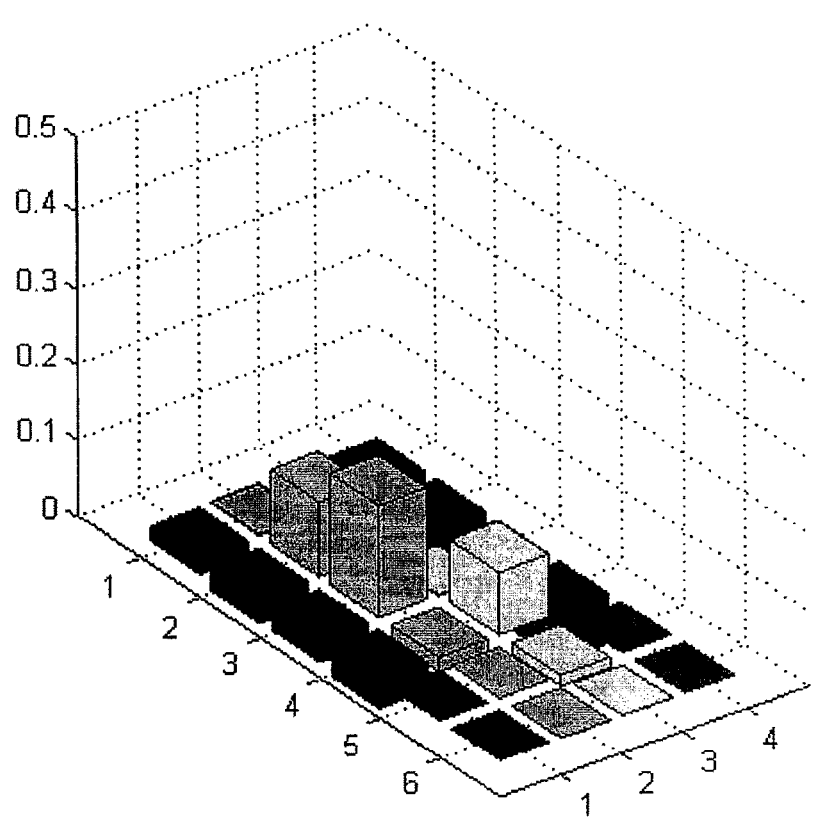
FIG. 12 shows a 3-D bar plot wherein each bar indicates a single taxel in a 24 taxel sensor when an object was placed on the surface of the sensor.

In test 4, an object was placed on the surface of the multi taxel tactile sensor. The result of contact indicates the capability of sensor to detect the shape of object. FIG. 12 shows a 3D bar plot where each bar indicates one taxel. At the time of contact taxels (I2-J2), (I2-J3) and (I3-J4) have increases in their signal amplitudes. This indicates the location of contact and force distribution at each taxel Test 5

In test 5, a Sharp object was slid over the sensor surface. Timing between the taxel signals showed the slip direction and speed. The graphs that were created show signal output from 24 taxels wherein upon sliding the object there were increases in signals first at various taxels which indicated the place of contact, the direction of motion, and the speed of motion was also calculated by the timing between when each taxel is triggered.

Test 6

Figure 13:
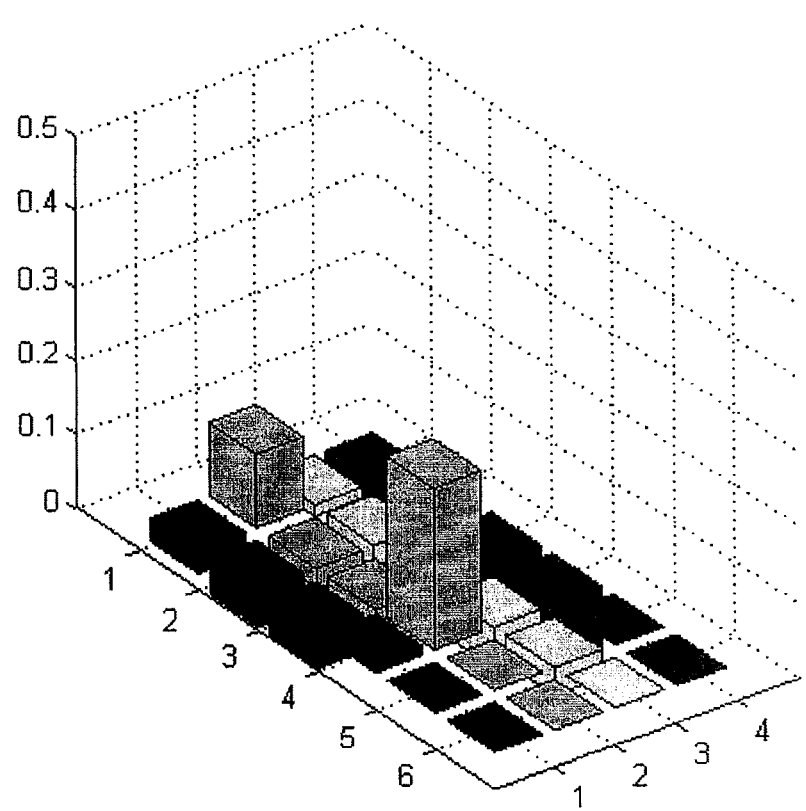
FIG. 13 shows a 3-D bar plot wherein each bar indicates a single taxel in a 24 taxel sensor when multiple objects were placed on the surface of the sensor

In test 6, an object was pressed on the sensor. An additional object was pressed in another location while the first object was on the touch with the sensor. FIG. 13 shows a 3D bar plot representing the amplitude of each taxel at each sampling time. In FIG. 13, upon the contact with an object, the taxel at (I2-J3) has increased its output voltage indicating the amplitude of the contact force. At the same time there are 2 different contacts at different locations and at different times. The second contact happened at location of the taxel at (I2-J6) and the third contact happened at location of the taxel at (I2-J5). Once there was still contact at the taxel at (I2-J3). FIG. 13 shows the 3D bar plot for the second contact which happened at the taxel at (I2-J6) while there was still contact at the taxel at (I2-J3).

Test 7

Figure 14:
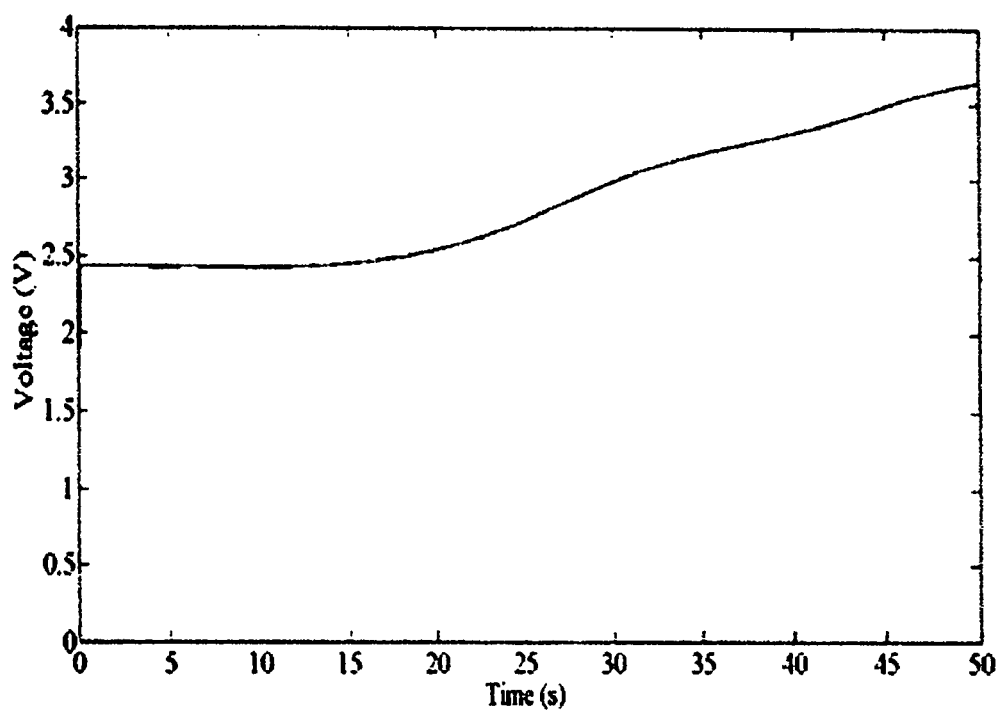
FIG. 14 shows the amplitude of the signal when an object having a temperature of 78° F. was pressed against a sensor having a temperature of 72° F.
Figure 15:
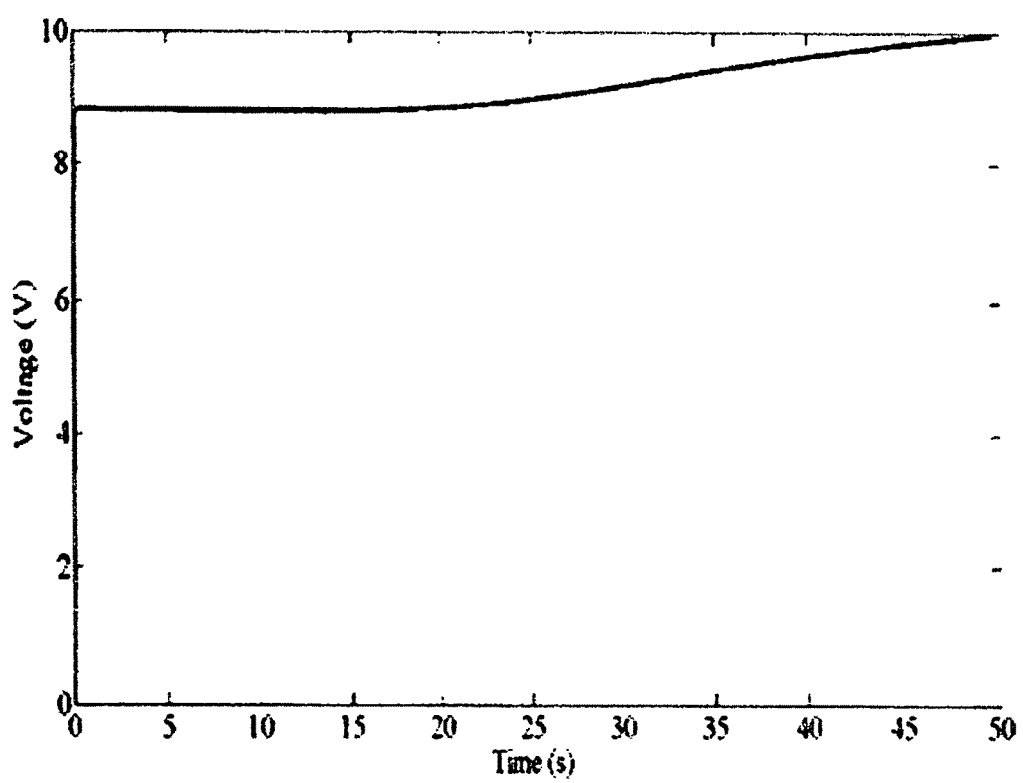
FIG. 15 shows the amplitude of the signal when an object having a temperature of 81° F. was pressed against a sensor having a temperature of 72° F.

In test 7, two warm objects, measuring temperatures of 78° F. and 81° F. respectively, were placed in contact with one of the sensor taxels separately. As shown in FIG. 14, the amplitude of the signal gradually increasing as the temperature increases from 72° F. to 78° F. FIG. 15 shows that the amplitude of the signal gradually increasing as the temperature increases from 72° F. to 81° F. This indicates the ability of the sensor in detecting the temperature.

Due to the lack of economic, flexible and mechanically compliant tactile sensors, a hybrid DW manufacturing process was developed to fabricate compliant tactile sensors. A micro-dispensing DW system was developed and dispensing parameters were experimentally investigated to create a predetermined wire size. Several sensors were produced by creating flexible conductive wires with a MWCNT/polymer composite on a layer of polyurethane rubber. Forces applied to the sensor were able to be consistently measured. The sensor was also shown to be sensitive to mechanical vibrations that occur during slip. These nonslip events could be distinguished from slip events with an FFT that showed a greater high frequency power spectral density characterizing the slip events. A four pole Chebyshev filter was designed to amplify the vibrations that occur during slip to distinguish between the two classes of tactile events. Hence, it is concluded that the suggested materials and manufacturing system for sensors are promising and the developed sensor has a wide range of applications for dexterous manipulation in robotics and prosthetics.

Figure 16:
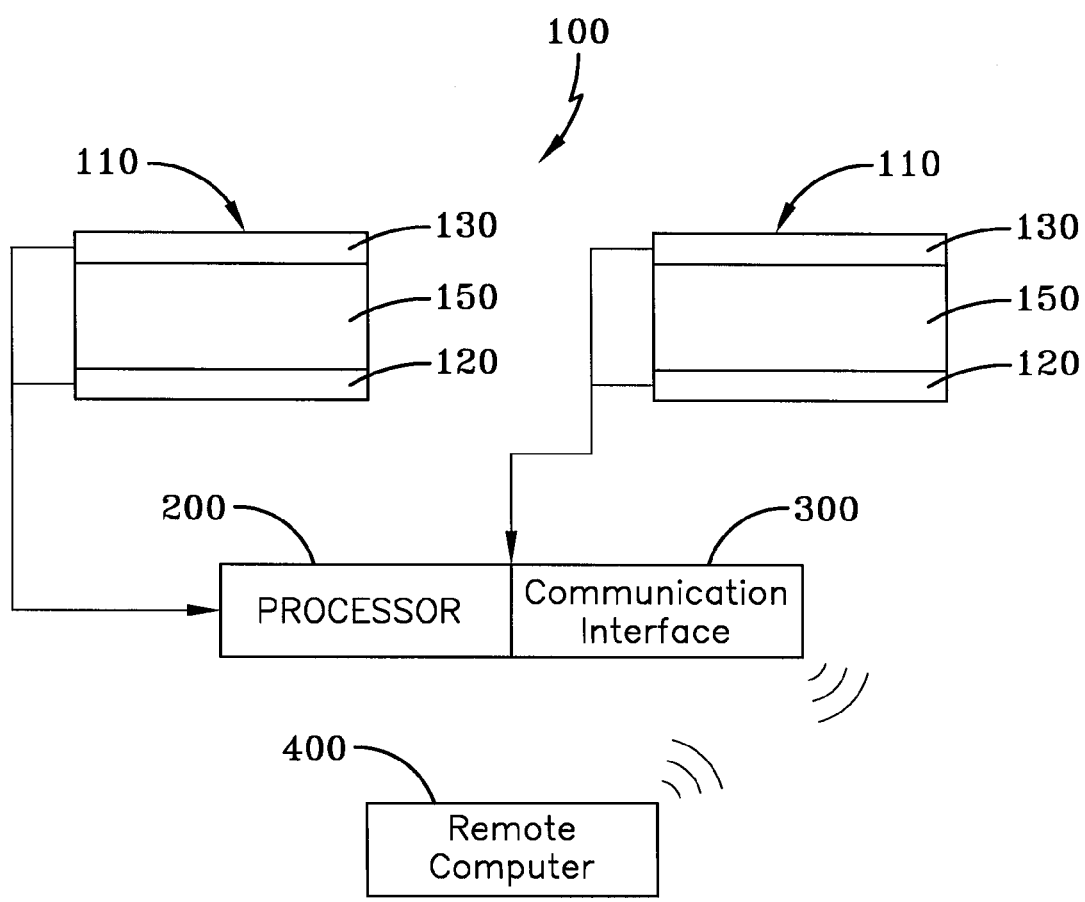
FIG. 16 shows a schematic view of a force sensor that utilizes one or more individual force sensing elements in accordance with one or more embodiments of the present invention.
Figure 17:
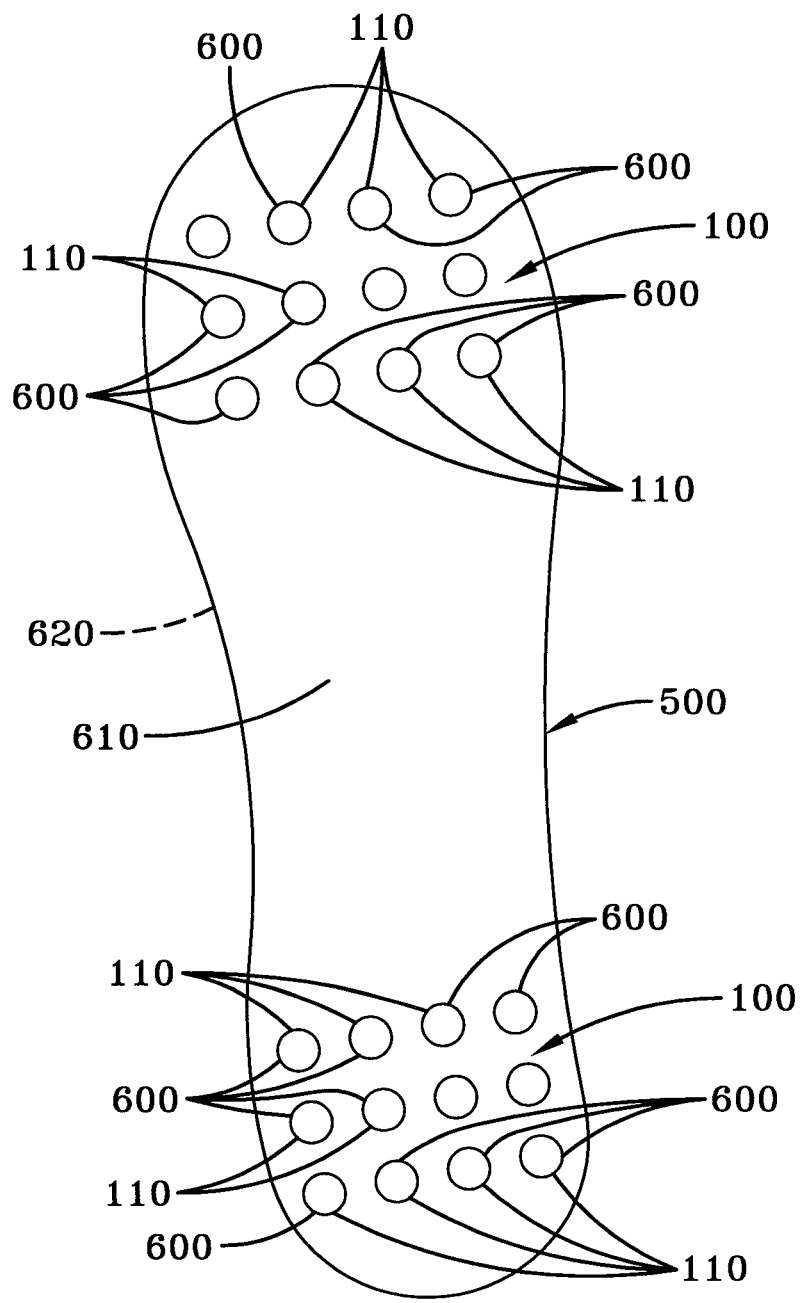
FIG. 17 shows an elevational view of the force sensing elements of the force sensor, which are utilized with a resilient substrate that is formed as an insole for a shoe, in accordance with one or more embodiments of the present invention.
Figure 18A:
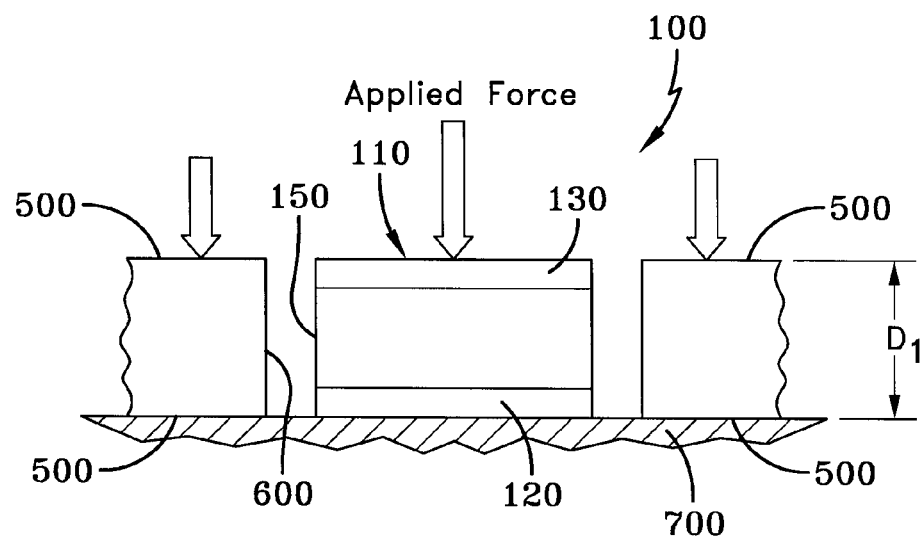
FIG. 18A shows a cross-sectional view of one force sensing element, which is utilized in conjunction with the shoe insole of FIG. 17 when no force is applied to the sensor, such that the force sensing element and the shoe insole are shown uncompressed, in a normal state, in accordance with one or more embodiments of the present invention.
Figure 18B:
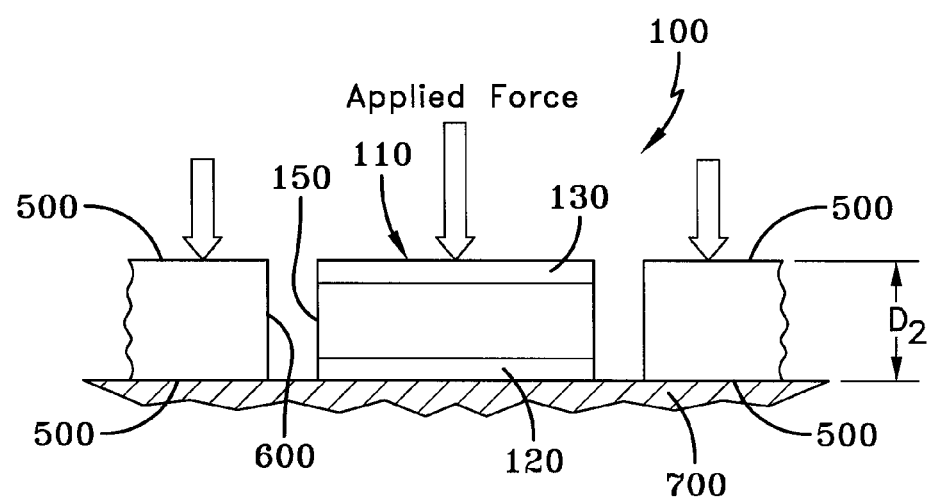
FIG. 18B shows a cross-sectional view of one force sensing element, which is utilized in conjunction with the shoe insole of FIG. 17 when an external force is applied to the sensor, such that the force sensing element and the shoe insole are shown being compressed from their normal state in accordance with one or more embodiments of the present invention.

In another embodiment, a force sensor 100, shown in FIGS. 16-18, may include one or more force sensing elements 110. Each force sensing element 110, shown clearly in FIG. 16, includes a pair of spaced electrodes 120 and 130, which are each positioned adjacent to a semiconductor layer or sensing layer 150 that is arranged between the electrodes 120,130.

It should be appreciated that in some embodiments, the electrodes 120 and 130 are positioned so as to be substantially opposite each other. As such, the electrodes 120 and 130, along with the sensing layer 150 may be formed as a laminated or layered structure. Furthermore, in some embodiments, the electrodes 120 and 130 may be positioned to be opposite one another along a common axis. Alternatively, the electrodes 120 and 130 may be positioned opposite to each other, but without being aligned along a common axis, so as to be offset relative to each other. In addition, in other embodiments, the electrodes 120 and 130, along with the sensing layer 150, may be positioned directly adjacent to each other so that they are not separated by any other intervening layers. However, in other embodiments, the electrodes 120 and 130, along with the sensing layer 150 may be separated from each other by one or more other intervening layers of any desired material.

It should also be appreciated that the electrodes 120 and 130 may be formed of any suitable electrically conductive material, such as silver, gold, copper, aluminum, or carbon for example. In addition, the electrodes 120 and 130 may be each formed, such as by printing for example, on a thin film. It should also be appreciated that the supporting electrical circuitry used for connection to the electrodes 120,130 to other electrical components used by the sensor 100 may also be formed, such as by printing, on these thin films as well. In some embodiments, the thin films may comprise polyethylene terephthalate (PET), or any other suitable material. Furthermore, because the thin films are each positioned on the outside of each electrode 120,130, so as to be directly adjacent or proximate to the external environment, the thin film serves as a protective layer over the electrodes 120,130 and the sensing elements 110.

The sensing layer 150 is formed of a polymerized acrylic semiconductor material, which may include any polymer/elastomer in which an ionic-liquid polymer can be dispersed. For example, in some embodiments, the polymerized acrylic semiconductor material of the sensing layer 150 may utilize monomers such as 2-[[(Butylamino)carbonyl]oxy]ethyl acrylate and/or 2-(2-Ethoxyethoxy)ethyl acrylate. These monomers may be cross-linked using any suitable cross-linking material and initiators, such as glyceryl propoxy triacrylate and/or Igracure 819 for example, in the presence of an ionic-liquid polymer, such as 1-Ethyl-3-methylimidazolium tetrafluoroborate. It should be appreciated that in some embodiments, the polymerized acrylic semiconductor material of the sensing layer 150 may be formed to have a composition or mixture that consists of: 82.5 wt % 2-[[(Butylamino)carbonyl]oxy]ethyl acrylate, 15 wt % 2-(2-Ethoxyethoxy)ethyl acrylate, 1.6 wt % glyceryl propoxy triacrylate, 0.4 wt % Igracure 819, and 0.5 wt % 1-Ethyl-3-methylimidazolium tetrafluoroborate. However, it should be appreciated that in other embodiments, the particular polymerized acrylic semiconductor material used by the sensing layer 150 discussed above may be configured to have a composition that includes one or more additional components or materials. Furthermore, in other embodiments, the polymerized acrylic semiconductor material of the sensing layer 150 discussed above may be formed using any suitable acrylic monomer or combination of acrylic monomers, and any suitable ionic-liquid polymer which is capable of being dispersed therein.

Next, the polymerized acrylic semiconductor material of the sensing layer 150, in the form of a mixture, is then cured as a substantially flat or planar sheet or section, which is then configured to be placed in the sensing element 110 previously discussed. It should be appreciated that the sensing element 110 may be formed to have any suitable thickness, such as from 0.1 mm to several millimeters, such as 3 mm.

It is also contemplated that the electrodes 120 and 130, along the with the sensing layer 150 forming the sensing element 110 may be formed to have any desired shape or thickness. For example, the sensing elements 110 may have a rectilinear shape, a curvilinear shape or a combination of both. In some embodiments, the sensing elements 110 have a round or square shape.

The force sensing elements 110 provided by the sensor 100 are each electrically coupled by their electrodes 120 and 130 to a data processor 200, as shown in FIG. 16. The processor 200 includes the necessary hardware, software or combination thereof to carry out the various functions of the sensor 100 discussed herein. In one embodiment, the processor 100 may comprise any suitable remote or local computing unit, including a standalone or portable computing unit, such as a wearable computing unit. In some embodiments, the processor 200 may comprise or include a Wheatstone bridge that is capable of detecting the changes in voltage levels output by the force sensing elements 110, however it should be appreciated that the processor 200 may comprise any suitable sensing device.

In other embodiments, the processor 200 may also include a communication interface 300 that is configured to wirelessly communicate with a remote computing unit 400, so as to transfer force data acquired from the sensor 100 to the remote computing unit 400. In one aspect, the communication interface 300 may communicate with the remote computing unit 400 using any suitable communication medium, such as radio frequency (RF) or infrared (IR) communication for example, and may use any suitable communication protocol, such as WIFI or BLUETOOTH for example. The remote computing unit 400 may include a standalone computing device, or a portable computing device, such as a smartphone, smartwatch, or any suitable wearable computing device.

It should also be appreciated that in other embodiments, the communication interface 300 may comprise a data port that is configured so that a portable storage device, such as a FLASH drive, may be removably or wirelessly attached or placed into communication with the communication interface 300 to allow the transfer of force data acquired from the sensor 100.

In other embodiments, the data processor 200 may include a GPS (global positioning sensor) sensor that is used to identify the position of the sensor 100 where the force is applied thereto, and at what time.

In addition, the sensor 100 may be used in conjunction with a substrate 500, as shown in FIG. 17. The substrate 500 may be formed out of any suitable resilient material, which is capable of returning to its original state after being compressed by a force. For example, the substrate 500 may be formed of rubber, such as NEOPRENE, HYPALON, polyurethane or silicone; or may be formed from a foam, such as polyurethane, polyethylene or ethylene vinyl acetate. Such materials used to from the substrate 500 may be configured to have any desired thickness and durometer (hardness). The substrate 500 may also include one or more cavities 600 disposed on an upper surface 610 of the substrate 500, which are each utilized to receive therein one or more sensing element 110. The cavities 600 may partially extend through the substrate, but do not extend all the way therethrough to the lower surface 620 of the substrate 500. However, in other embodiments, the cavities 600 may comprise an aperture or hole that extends all the way through the substrate 500 so as to connect the upper surface 610 to the lower surface 620 of the substrate 500. One or more cavities 600 may be arranged or positioned with respect to the substrate 500 in any desired manner depending on the particular location of the force that is desired to be measured with the sensor 100. Furthermore, the hardness (i.e. durometer) of the substrate 500 is calibrated to be sufficient to allow the sensing elements 110 to be compressed by an application of a force thereto, while preventing the sensing elements 110 from being compressed beyond a maximum threshold. This ability to allow both the safe compression of the sensing elements 110 up to a maximum threshold or limit, serves to establish a safe operating range for the sensing elements 110. This ensures that the sensing elements 110 are not physically damaged by applied forces that exceed the safe range of the sensing element 110, which could damage the ability of the sensor layer 150 to continue to accurately detect force.

Thus, in one embodiment, the sensor 100 may be configured with one or more sensing elements 110 positioned in corresponding cavities 600 in the substrate 500, which is formed as a shoe insole, as shown in FIG. 17. However, in other embodiments, the substrate 500 may be formed as an insert, which could be inserted on top of, or underneath, the insole of a shoe in order to monitor the force changes that occur during the movement of the wearer of the shoe. For example, due to the force sensing ability of the sensing elements 110, the sensor 100 is able to record the number of foot strikes that occur as a person walks or runs over a certain distance. In addition to recording the number of foot strikes, the force sensor 11, via the processor 200, is able to compute the total distance a person has walked, run, or otherwise moved, as well as their cadence using known techniques. Furthermore, when multiple or a plurality of sensing elements 110 are used by the sensor 100, a visual map showing the different forces that are applied over different parts of the person's foot as he or she moves can be achieved using a suitable display, which may be part of, or in communication with, the remote computing unit 400 or the processor 200.

It should be appreciated, that the cavities 600 may be open, enclosed to encapsulate each sensing element 110, or may be partially enclosed while still providing support for the sensing elements 110 therein.

Accordingly, during operation of the sensor 100 the substrate 500 and the sensing elements 110 are supported by a rigid surface 700, such as the bottom of the interior of a shoe or any other surface. Next, the sensing layer 150 of the sensing element 110 is initially in an uncompressed state, shown by reference character "$D_1$" in FIG. 18A. However, it should be appreciated that the sensor 100 may be configured to identify the application of baseline force, such as when a person is only standing upon the sensor 100 and not moving (i.e. static), as an uncompressed state. Next, upon the application of a force, such as that applied by a person's foot as he or she moves, as discussed above, the sensing layer 150 of the sensing element 110 is compressed, shown by reference character "$D_2$" in FIG. 18B. This causes the semiconducting layer to generate a voltage value that corresponds to the amount of force applied to the sensing element 110. This voltage value and/or change in voltage values are then detected and recorded by the processor 200, or in some embodiments transmitted by the processor 200 to the remote computing device 400 for further analysis and processing. As such, the voltage data representing the corresponding force applied to a specific sensing element 110 is able to be processed by the processor 200 and/or the remote computing unit 400 and converted into an applied force measurement value. It should be appreciated, that the conversion of an identified voltage value from the sensing element 110 into a corresponding applied force measurement value may be performed using any suitable technique. For example, one such technique may include calibrating the sensing element 110, by establishing a look-up table of identified or pre-measured voltage values and corresponding force values for example. Thus, an applied force measurement value is identified using the look-up table based on the voltage that is generated from the sensing element 110 to which a physical force is applied.

Using, the force measurement values from one or more sensing elements 110, the sensor 100 is able to monitor the movement of the person's feet, and is able to measure a variety of movement parameters associated with the movement of the person, including their pace or cadence, speed, distance traveled, etc. It should be appreciated that these movement parameters or data may be computed at the processor 200 and presented on a suitable display, such as a wearable LCD (liquid crystal display) provided by a smartwatch or other wearable or portable display. Or alternatively, the movement parameters may be computed at the processor 200 and stored for retrieval via the communication interface 300. Furthermore, the voltage data associated with a measured force may be communicated to the remote computer 400 in the various manners previously discussed, whereupon the specific movement parameters are computed by the remote computer 400 and presented on any suitable output device, such as an LCD display.

It should be appreciated that the sensor 100 and substrate 500, while discussed herein as being used in connection with a shoe, may be configured for use with any desired application in which a force measurement is desired.

In light of the foregoing, it should be appreciated that the present invention significantly advances the art by providing an improved and flexible tactile sensor. While particular embodiments of the invention have been disclosed in detail herein, it should be appreciated that the invention is not limited thereto or thereby inasmuch as variations on the invention herein will be readily appreciated by those of ordinary skill in the art. The scope of the invention shall be appreciated from the claims that follow.

What is claimed is:

1. A tactile sensor comprising:
a first insulating layer having a first array of electrically conductive strips embedded therein and extending in a first direction,
an intermediate layer of conductive soft polymer material positioned above said first insulating layer and first array of said electrically conductive strips, and
a second insulating layer having a second array of electrically conductive strips embedded therein and extending in a second direction which is different than said first direction positioned above said intermediate layer, wherein said first array of electrically conductive strips are connected to said second array of electrically conductive strips, and wherein both the first and second array of electrically conductive strips are connected to an impedance measuring device, wherein the conductive soft polymer material is an ionic liquid polymer, and wherein the weight percent of the ionic liquid based upon the total weight of the ionic liquid polymer within the intermediate layer is selected from the group consisting of from 0.01 or more to 10 or less weight percent (wt %) of ionic liquid, from 0.05 or more to 7.5 or less weight percent (wt %) ionic liquid, from 0.5 or more to 5 or less weight percent (wt %) ionic liquid, and from 1 or more to 2.5 or less weight percent (wt %) ionic liquid.

2. The tactile sensor of claim 1, wherein said first and second arrays of electrically conductive strips include conductive nanostructures dispersed in a flexible support material, wherein said conductive nanostructures are selected from the group consisting of conductive nanowires, carbon nanotubes, and graphene, and wherein said carbon nanotubes are selected from the group consisting of multi-walled carbon nanotubes or single wall carbon nanotubes.

3. The tactile sensor of claim 2, wherein said electrically conductive strips contain from 0.01 wt % to 20 wt % carbon nanotubes and wherein said carbon nanotubes have an average length from 300 nanometers to 30 microns.

4. The tactile sensor of claim 1, wherein the ionic liquid polymer is selected from the group consisting of 1-ethyl-3-methylimidazolium tetrafluoroborate (EMIBF4) with the Tg of −95.15° C.; 1-ethyl-3-methylimidazolium bis(trifluoromethylsulfonyl)imide (EMITFSI) with the Tg of −98.15° C.; and 1-butylpyridinium tetrafluoroborate (BPBF4) with the Tg of −66.7°C.

5. The tactile sensor of claim 1, wherein the ionic liquid polymer is a pressure sensitive polymer.

6. The tactile sensor of claim 1, wherein said second direction of said second array of electrically conductive strips is off of parallel as compared to said first direction of said first array and wherein said impedance measuring device is a Wheatstone bridge.

7. The tactile sensor of claim 1, wherein said first insulating layer and said second insulating layer is stretchable.

8. The tactile sensor of claim 1, wherein said first insulating layer and said second insulating layer comprise material selected from group consisting of elastomers, polymers, and thermoplastics, wherein the elastomers are selected from the group consisting of polyepoxides rubber, natural polyisoprene, synthetic polyisoprene, polybutadiene, chloroprene rubber, butyl rubber, styrene-butadiene rubber, nitrile rubber, ethylene propylene rubber, epichlorohydrin, polyacrylic rubber, silicone rubber, fluoresilicone, fluoroelastomers, perfluorelastomers, polyether block amines, chlorosulfonated polyethylene, ethylene-vynyl acetate, thermoplastic elastomer, polyurethane, and mixtures thereof, and wherein said material of said first insulating layer can be the same or different than the material of the second insulating layer.

9. The tactile sensor of claim 1, wherein the tactile sensor detects:
(a) applied force such as normal and shear forces,
(b) the proximity of the applied force,
(c) slip events,
(d) slip direction,
(e) slip speed,
(f) slip velocity,
(g) temperature changes,
(h) rolling contact,
(i) the shape of an object in contact with said tactile sensor, and
(j) vibration.

10. A sensor comprising:
a first electrode;
an intermediate layer formed of ionic liquid material dispersed in a polymer material, said intermediate layer positioned adjacent to said first electrode; and
a second electrode positioned adjacent to said intermediate layer,
wherein said intermediate layer is formed by polymerizing monomers in the presence of an ionic-liquid polymer.

11. The sensor of claim 10, wherein said first electrode and said second electrodes are each carried on a film.

12. The sensor of claim 10, wherein said first and second electrodes are positioned on opposite sides of said intermediate layer.

13. The sensor of claim 12, wherein said first and second electrodes are aligned along a common axis.

14. The sensor of claim 12, wherein said first and second electrodes are offset relative to each other.

15. The sensor of claim 10, further comprising:
a substrate formed of resilient material having at least one cavity in which at least one said sensor is positioned therein, whereby said substrate limits the maximum amount said intermediate layer is permitted to be compressed by a force.

16. The sensor of claim 15, wherein said at least one cavity comprises a plurality of cavities.

17. The sensor of claim 15, wherein said at least one cavity forms an opening between a first surface of said substrate and a second surface of said substrate.

18. The sensor of claim 15, wherein said at least one cavity is closed to encapsulate said at least one sensor therein.

19. The sensor of claim 15, wherein said at least one cavity at least partially supports said sensor disposed therein.

20. The sensor of claim 15, wherein said substrate comprises a shoe insert.

21. The sensor of claim 10, wherein said electrodes are coupled to a an impedance measuring device.

22. The sensor of claim 21, wherein said impedance measuring device is coupled to a communication interface to communicate said voltage value and a time value.

23. The sensor of claim 22, wherein said communication interface is a wireless communication interface.

24. The sensor of claim 10, wherein said intermediate layer includes an ionic-liquid polymer having a concentration from 0.05 wt % to 10 wt %.

25. The sensor of claim 24, wherein said ionic-liquid polymer comprises 1-ethyl-3-methylimidazolium tetrafluoroborate (EMIBF4), 1-ethyl-3-methylimidazolium bis(trifluoromethylsulfonyl)imide (EMITFSI) or 1-butylpyridinium tetrafluoroborate (BPBF4).

26. The sensor of claim 10, wherein said polymer material comprises an elastomer material.

27. The sensor of claim 10, wherein said monomers comprise acrylic monomers.

28. The sensor of claim 27, wherein said acrylic monomers include 2-[[(Butylamino)carbonyl]oxy]ethyl acrylate and 2-(2-Ethoxyethoxy)ethyl Acrylate.

29. The sensor of claim 10, wherein said monomers are polymerized with glyceryl propoxy triacrylate and Irgacure 819.

30. The sensor of claim 10, wherein said ionic-liquid polymer comprises 1-Ethyl-3-methylimidazolium tetrafluoroborate.

31. A sensor comprising:
a first electrode;
an intermediate layer formed of ionic liquid material dispersed in a polymer material, said intermediate layer positioned adjacent to said first electrode; and a second electrode positioned adjacent to said intermediate layer,
wherein said intermediate layer is formed by polymerizing a 2- [[(Butylamino)carbonyl]oxy]ethyl acrylate material and a 2-(2-Ethoxyethoxy)ethyl Acrylate material using a glyceryl propoxy triacrylate material and an Irgacure 819material in the presence of a 1-Ethyl-3-methylimidazolium tetrafluoroborate material.

32. The sensor of claim 31, wherein said materials have respective concentrations of 82.5 wt %, 15 wt %, 1.6 wt %, 0.4 wt % and 0.5 wt %.

33. A sensor comprising:
a sensing element comprising:
a first electrode;
an intermediate layer of semiconductor polymer material positioned adjacent to said first electrode; and
a second electrode positioned adjacent to said intermediate layer;
a substrate formed of resilient material having at least one cavity in which at least one said sensing element is positioned, whereby said substrate limits the maximum amount said intermediate layer is permitted to be compressed,
wherein said intermediate layer is formed by polymerizing monomers in the presence of an ionic-liquid polymer.

34. The sensor of claim 33, wherein said first and said second electrodes are coupled to an impedance measuring device.

35. The sensor of claim 34, wherein said impedance measuring device is coupled to a communication interface to communicate said voltage value and a time value.

36. The sensor of claim 35, wherein said communication interface is a wireless communication interface.

37. The sensor of claim 33, wherein said at least one cavity comprises a plurality of cavities.

38. The sensor of claim 33, wherein said at least one cavity forms an opening between a first surface of said substrate and a second surface of said substrate.

39. The sensor of claim 33, wherein said at least one cavity is closed to encapsulate said at least one sensor therein.

40. The sensor of claim 33, wherein said at least one cavity at least partially supports said sensor disposed therein.

41. The sensor of claim 33, wherein said substrate comprises a shoe insert.

42. The sensor of claim 33, wherein said semiconductor polymer material is elastomeric.

43. The sensor of claim 33, wherein said semiconductor polymer material comprises an ionic liquid material dispersed in a polymer material.

44. The sensor of claim 43, wherein said ionic-liquid polymer has a concentration from 0.05 wt % to 10 wt %.

45. The sensor of claim 44, wherein said ionic-liquid polymer comprises 1-ethyl-3-methylimidazolium tetrafluoroborate (EMIBF4), 1-ethyl-3-methylimidazolium bis(trifluoromethylsulfonyl)imide (EMITFSI) or 1-butylpyridinium tetrafluoroborate (BPBF4).

46. The sensor of claim 43, wherein said polymer material comprises an elastomer material.

47. The sensor of claim 33, wherein said monomers comprise acrylic monomers.

48. The sensor of claim 47, wherein said acrylic monomers include 2-[[(Butylamino)carbonyl]oxy]ethyl acrylate and 2-(2-Ethoxyethoxy)ethyl Acrylate.

49. The sensor of claim 33, wherein said monomers are polymerized with glyceryl propoxy triacrylate and Irgacure 819.

50. The sensor of claim 33, wherein said ionic-liquid polymer comprises 1-Ethyl-3-methylimidazolium tetrafluoroborate.

51. A sensor comprising:
a sensing element comprising:
a first electrode;
an intermediate layer of semiconductor polymer material positioned adjacent to said first electrode; and
a second electrode positioned adjacent to said intermediate layer;
a substrate formed of resilient material having at least one cavity in which at least one said sensing element is positioned, whereby said substrate limits the maximum amount said intermediate layer is permitted to be compressed,
wherein said intermediate layer is formed by polymerizing a 2- [[(Butylamino)carbonyl]oxy]ethyl acrylate material and a 2-(2-Ethoxyethoxy)ethyl Acrylate material using a glyceryl propoxy triacrylate material and a Irgacure 819material in the presence of a 1-Ethyl-3-methylimidazolium tetrafluoroborate material.

52. The sensor of claim 51, wherein said materials have respective concentrations of 82.5 wt %, 15 wt %, 1.6 wt %, 0.4 wt % and 0.5 wt %.

* * * * *